(12) United States Patent
Ariav et al.

(10) Patent No.: US 7,533,571 B2
(45) Date of Patent: May 19, 2009

(54) APPARATUS FOR MAKING HIGH-SENSITIVITY MEASUREMENTS OF VARIOUS PARAMETERS, AND SENSORS PARTICULARLY USEFUL IN SUCH APPARATUS

(75) Inventors: Arie Ariav, Doar-Na Hof Ashkelon (IL); Vladimir Ravitch, Ashkelon (IL)

(73) Assignee: Nexense Ltd., Yavne (IL)

( * ) Notice: Subject to any disclaimer, the term of this patent is extended or adjusted under 35 U.S.C. 154(b) by 280 days.

(21) Appl. No.: 10/545,386

(22) PCT Filed: Feb. 12, 2004

(86) PCT No.: PCT/IL2004/000138

§ 371 (c)(1),
(2), (4) Date: Aug. 12, 2005

(87) PCT Pub. No.: WO2004/072658

PCT Pub. Date: Aug. 26, 2004

(65) Prior Publication Data

US 2006/0087325 A1    Apr. 27, 2006

Related U.S. Application Data

(60) Provisional application No. 60/447,017, filed on Feb. 13, 2003, provisional application No. 60/483,110, filed on Jun. 30, 2003.

(51) Int. Cl.
*G01N 29/00* (2006.01)
(52) U.S. Cl. .......................................... 73/597; 73/602
(58) Field of Classification Search ................ 73/597, 73/602; 324/639, 204, 698, 598
See application file for complete search history.

(56) References Cited

U.S. PATENT DOCUMENTS

| | | | | |
|---|---|---|---|---|
| 3,381,267 | A * | 4/1968 | Cubberly, Jr. et al. | 367/189 |
| 4,395,451 | A * | 7/1983 | Althouse | 428/141 |
| 5,392,635 | A | 2/1995 | Cadet et al. | |
| 5,935,073 | A | 8/1999 | Wilson et al. | |
| 6,131,002 | A * | 10/2000 | Gibson et al. | 399/57 |
| 6,352,512 | B1 * | 3/2002 | Wilson et al. | 600/449 |
| 6,571,632 | B1 | 6/2003 | Browner et al. | |
| 6,621,278 | B2 * | 9/2003 | Ariav | 324/637 |
| 6,926,679 | B2 * | 8/2005 | Friedrichs | 600/588 |
| 6,984,993 | B2 * | 1/2006 | Ariav | 324/639 |
| 2004/0240897 | A1 * | 12/2004 | Chou et al. | 399/29 |
| 2005/0215335 | A1 * | 9/2005 | Marquardt | 473/131 |
| 2005/0279164 | A1 * | 12/2005 | Ploechinger | 73/488 |

* cited by examiner

*Primary Examiner*—Hezron Williams
*Assistant Examiner*—J M Saint Surin

(57) ABSTRACT

A sensor for sensing a predetermined parameter having a known relationship with respect to the transit time of an energy wave through a medium, includes a body of soft elastomeric material having high transmissivity and low attenuation properties with respect to the energy waves; and a transmitter and receiver carried by the body in spaced relation to each other such that the energy waves received by the receiver are those transmitted by the transmitter after having traversed at least a portion of the body of soft elastomeric material. The transit time of the energy wave through the elastomeric body is measured to produce a measurement of the predetermined parameter. In the described preferred embodiments, the energy wave is a sonic wave, such that the body of soft elastomeric material serves as an acoustical channel between the transmitter and receiver.

27 Claims, 17 Drawing Sheets

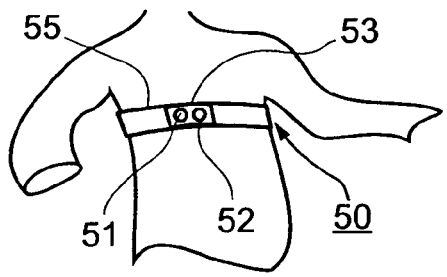
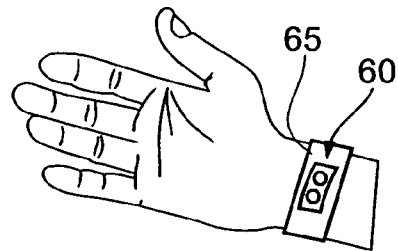
Fig. 5
Fig. 6
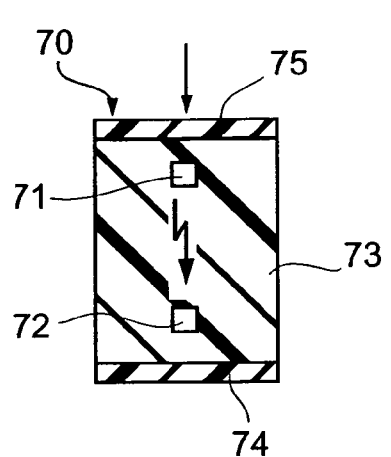
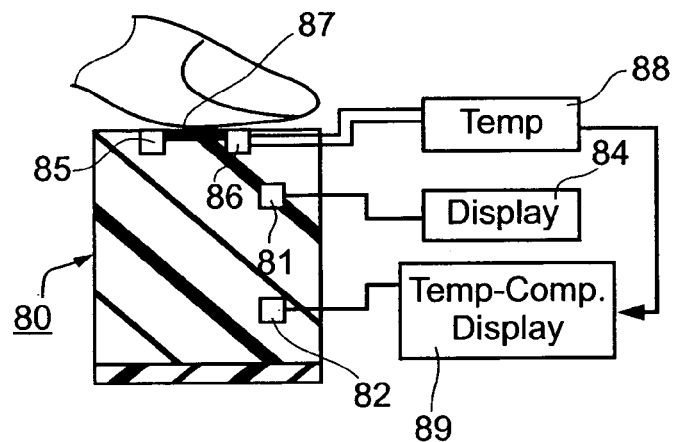
Fig. 7
Fig. 8
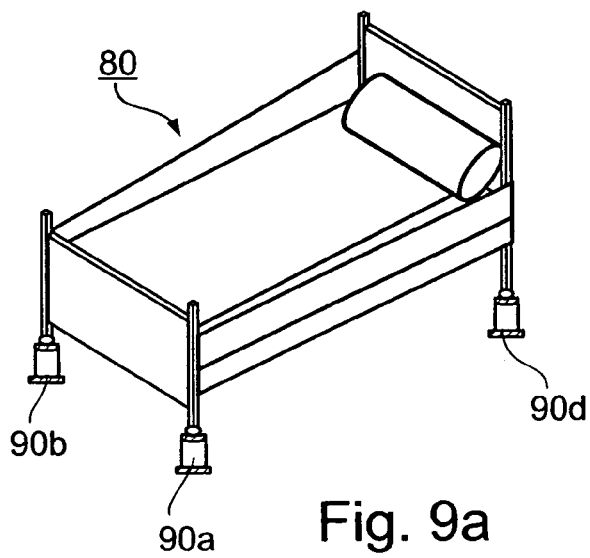
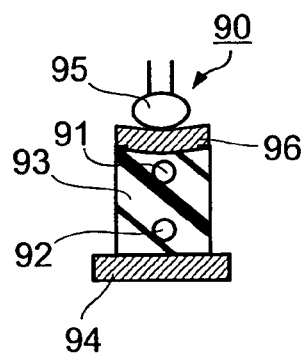
Fig. 9a
Fig. 9b

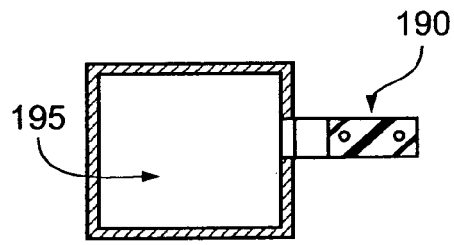
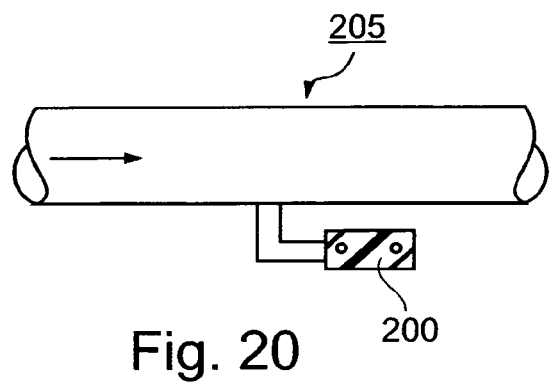
Fig. 19        Fig. 20
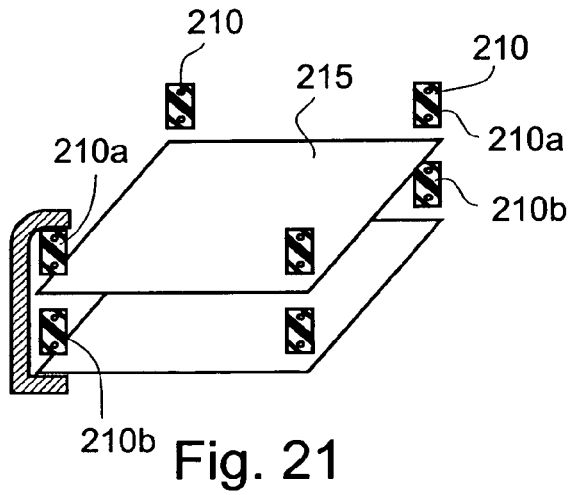
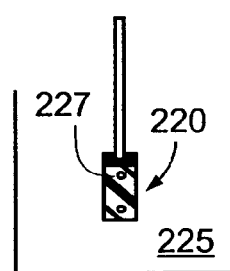
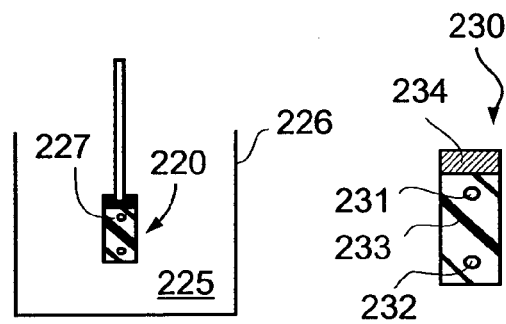
Fig. 21        Fig. 22        Fig. 23
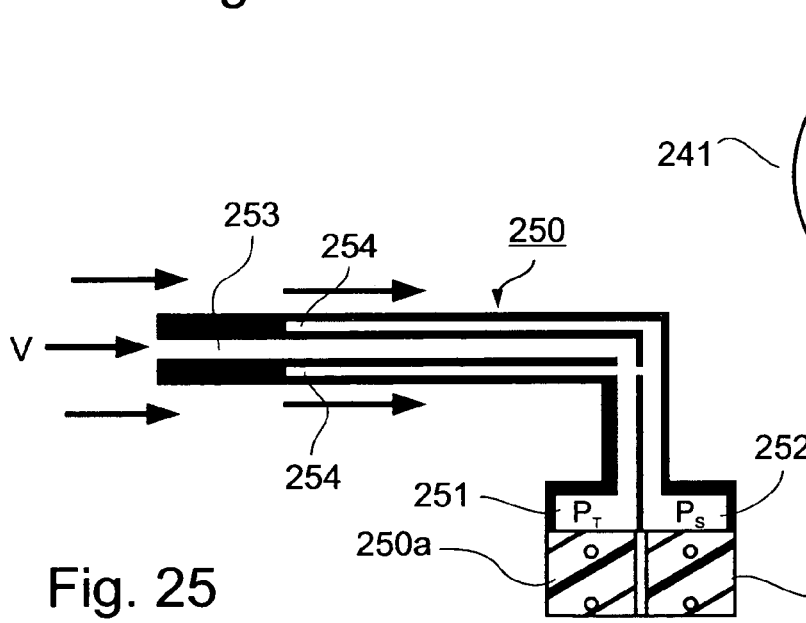
Fig. 24
Fig. 25

APPARATUS FOR MAKING HIGH-SENSITIVITY MEASUREMENTS OF VARIOUS PARAMETERS, AND SENSORS PARTICULARLY USEFUL IN SUCH APPARATUS

RELATED PATENT APPLICATION

This application is a National Phase Application of PCT/IL2004/000138 having International Filing Date of 12 Feb. 2004, which claims the benefit of U.S. Provisional Patent Application No. 60/447,017 filed 13 Feb. 2003 and the benefit of U.S. Provisional Application No.60/483,110, filed 30 Jun. 2003. The contents of the above Application are all incorporated herein by reference.

FIELD AND BACKGROUND OF THE INVENTION

The present application is related to: International Application PCT/IL00/00241 published Nov. 9, 2000 as International Publication No. WO 00/67013; International Application PCT/IL02/00854 filed Oct. 24, 2002, Published May 1, 2003 as International Publication No. WO 03/036321; International Application PCT/IL02/00983, filed Dec. 5, 2002, published Jun. 12, 2003 as International Publication No. WO 03/048668; and U.S. Pat. No. 6,621,278 issued Sep. 16, 2003, the contents of which applications and patent are incorporated herein by reference in their entirety.

The above-cited applications and patent relate to methods and apparatus for measuring, with extremely high sensitivity, various parameters having a known or determinable relationship with respect to the transit time of an energy wave (electromagnet or sonic) through a medium (solid, liquid or gas). Briefly, this is done by transmitting through the medium a cyclically-repeating energy wave; receiving the energy wave transmitted through the medium; detecting a predetermined fiducial point in the received energy wave; continuously changing the frequency of the transmission of the energy wave in accordance with the detected fiducial point of each received energy wave such that the number of waves received is a whole integer; and measuring the changes in frequency to produce a measurement of changes in transit time of the energy wave from the transmitter to the receiver, and thereby a measurement of the predetermined parameter.

The above-cited applications and patent described many implementations of such a method and apparatus in many fields, both medical and non-medical, for providing measurements having an extremely high degree of sensitivity. The described implementations included those which produced changes in the transit distance, and/or energy velocity in accordance with changes in the predetermined parameter measured. Various types of sensors were also described for measuring changes in the transit distance, including deformable membranes, bellows, spring-mounted members, and displaceable plungers.

OBJECTS AND BRIEF SUMMARY OF THE PRESENT INVENTION

An object of the present invention is to provide such apparatus with a new type of sensor making the apparatus particularly sensitive for measuring displacements with extremely high sensitivity thereby enabling the apparatus to accurately detect virtually any condition, or measure virtually any parameter, inducing, induced by, or otherwise accompanying a displacement. Examples of conditions so detected are very quick or small motions accompanying respiration and heart activity; and examples of parameters so measured, as described below, include pressure, torsion, linear acceleration, weight, temperature, angular velocity, linear velocity, liquid density, depth in a body of liquid, magnetic field strength, respiration rate, blood pulse rate and blood pressure.

Another object of the present invention is to provide a novel sensor particularly useful in such apparatus.

According to one aspect of the present invention, there is provided apparatus for measuring a predetermined parameter having a known or determinable relationship with respect to the transit time of an energy wave through a medium, comprising: a sensor for sensing the predetermined parameter, the sensor including a transmitter for transmitting energy waves through the medium and a receiver for receiving the energy waves transmitted by the transmitter; and a data processor for measuring the transit time, or changes in the transit time, of energy waves from the transmitter to the receiver to thereby produce a measurement of the predetermined parameter; characterized in that the sensor includes a body of soft elastomeric material having high transmissivity and low attenuation properties with respect to the energy waves, the transmitter and receiver being embedded in spaced relation to each other, in said body of soft elastomeric material such that the parameter, when sensed by the sensor, produces a displacement of the transmitter relative to the receiver, whereby measuring the transit time, or changes in the transit time, of the energy waves from the transmitter to the receiver provides a measurement of the displacement of the transmitter relative to the receiver, and thereby of the predetermined parameter.

The invention is particularly useful, and is therefore described below, with respect to applications in which the energy waves are sonic waves, whereby the transmission channel between the transmitter and receiver is an acoustical channel. It will be appreciated, however, that the invention could also be implemented in applications where the energy waves are electromagnetic waves, e.g., light, infra-red or RF, particularly when the modulating technique described for example in U.S. Pat. No. 6,621,278 is used.

According to another aspect of the present invention, there is provided a sensor for sensing a predetermined parameter having a known or determinable relationship with respect to the transit time of an energy wave through a medium, comprising: a body of soft elastomeric material having high transmissivity and low attenuation properties with respect to the energy waves; and a transmitter and receiver embedded within the body in spaced relation to each other such that the energy waves received by the receiver are those transmitted by the transmitter after having traversed at least a portion of the body of soft elastomeric material.

As will be described more particularly below, particularly good results are obtainable when sonic waves are used and the elastomeric material is a silicone elastomer having a Shore A hardness of 5-40, preferably 7-20. A Shore A hardness of about 10 was found most preferred in the applications described below.

Other aspects, advantages and applications of the invention are described below.

BRIEF DESCRIPTION OF THE DRAWINGS

The invention is herein described, by way of example only, with reference to the accompanying drawings, wherein:

FIGS. 5-8 illustrate further constructions of sensors in accordance with the present invention and several applications of such sensors;

FIGS. 9a-9c illustrate further applications of the present invention for detecting cessation of breathing (apnea detector), or for detecting movements, respiration, pulse rate, or other conditions of an individual;

FIGS. 19 and 20 illustrate the invention embodied in a pressure gauge for indicating the pressure in a pressurized container and pipe line, respectively;

FIG. 21 illustrates in the invention embodied in a scale for weighing objects;

FIG. 22 illustrates the invention embodied in an immersible sensor for measuring the density of the liquid in which it is immersed, or the depth at which the sensor is immersed;

FIG. 23 illustrates the invention embodied in a magnetic field sensor for measuring the strength of a magnetic field;

FIG. 24 illustrates the invention embodied in an instrument for measuring angular velocity and/or tangential acceleration of a rotating body;

FIG. 25 illustrates the invention embodied in a Pitot tube for measuring the velocity of an object through a fluid medium;

FIG. 40b is a three-dimensional view illustrating the securing device in the sensor of FIG. 40a;

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

As indicated earlier, the present invention relates to apparatus for measuring a parameter directly related to the displacement of one member with respect to another member, and particularly to a novel sensor for use in such apparatus. The parameter to be measured may be pressure, torque, tension, linear acceleration, angular velocity, temperature, weight, liquid density, liquid depth, magnetic field strength, respiration, blood pulse, or virtually any other parameter inducing, induced by, or otherwise accompanying a change in the transit time of an energy wave through a solid, liquid or gas medium.

The invention particularly provides a novel sensor which is capable of measuring the respective parameter by detecting a displacement with an extremely high degree of sensitivity. The novel sensor provides an energy-transmission channel which includes a body of soft elastomeric material, preferably a silicone elastomer, having high energy-transmissivity and low energy attenuation properties, a transmitter, and a receiver in spaced relationship to each other such that precisely measuring the change in the transit time of energy waves through the transmission channel from the transmitter to the receiver produces a precise measurement of the respective parameter.

In the preferred embodiments of the invention described below, the energy wave is a sonic wave, such that the transmission channel is an acoustical channel. It will be appreciated, however, that the energy wave could also be an electromagnetic wave, such as light, infra-red, RF, etc., particularly when the modulating technique described in the above-cited U.S. Pat. No. 6,621,278 is used.

Some embodiments described below are displacement-type sensors, wherein a displacement is sensed and measured; whereas other described embodiments are acceleration-type sensors, wherein the rate of change of a displacement is detected and measured.

Figure 1:
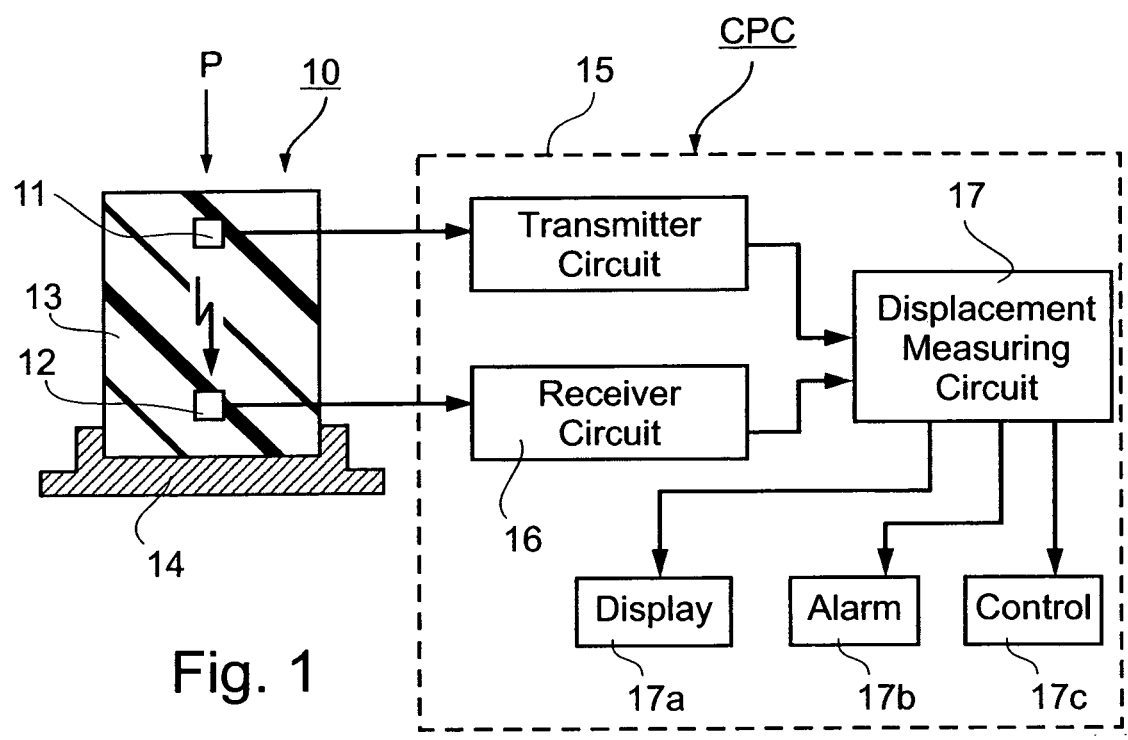
FIG. 1 is a block diagram broadly illustrating measuring apparatus including one form of sensor in accordance with the present invention.

FIG. 1 is block diagram broadly illustrating one form of apparatus constructed in accordance with the invention. The illustrated apparatus includes a sensor 10 having one face exposed to the parameter, in this case pressure, to be measured, as shown by arrow P. Sensor 10 includes a sonic transmitter 11 and a sonic receiver 12 embedded in spaced relationship within a body of soft, pressure-compressible elastomeric material, generally designated 13. The opposite face of sensor 10, i.e., opposite to that receiving the pressure P, is engaged by, or mounted on, a relatively rigid supporting member or base 14 such that the application of the pressure P will displace transmitter 11 towards receiver 12 in accordance with the magnitude of the applied pressure. Sensor 10 is thus a displacement-type sensor in that measuring the displacement or relative position of transmitter 11 with respect to receiver 12 will produce a precise measurement of the pressure P.

The position of transmitter 11 with respect to receiver 12 is precisely measured in accordance with the method and apparatus described in the above-cited International Applications and U.S. patent. Thus, the apparatus includes control and processor circuitry, generally designated CPC, for controlling the transmitter 11 and receiver 12 such as to produce a precise measurement of the change in relative positions between the two. The control and processor circuitry CPC shown in FIG. 1, and more particularly described below with respect to FIG. 2, includes a transmitter circuit 15, a receiver circuit 16, and a displacement measurement circuit 17 measuring the change in spacing between transmitter 11 and receiver 12, and producing an output, e.g., to a display 17a, an alarm 17b, and/or a control 17c.

Figure 2:
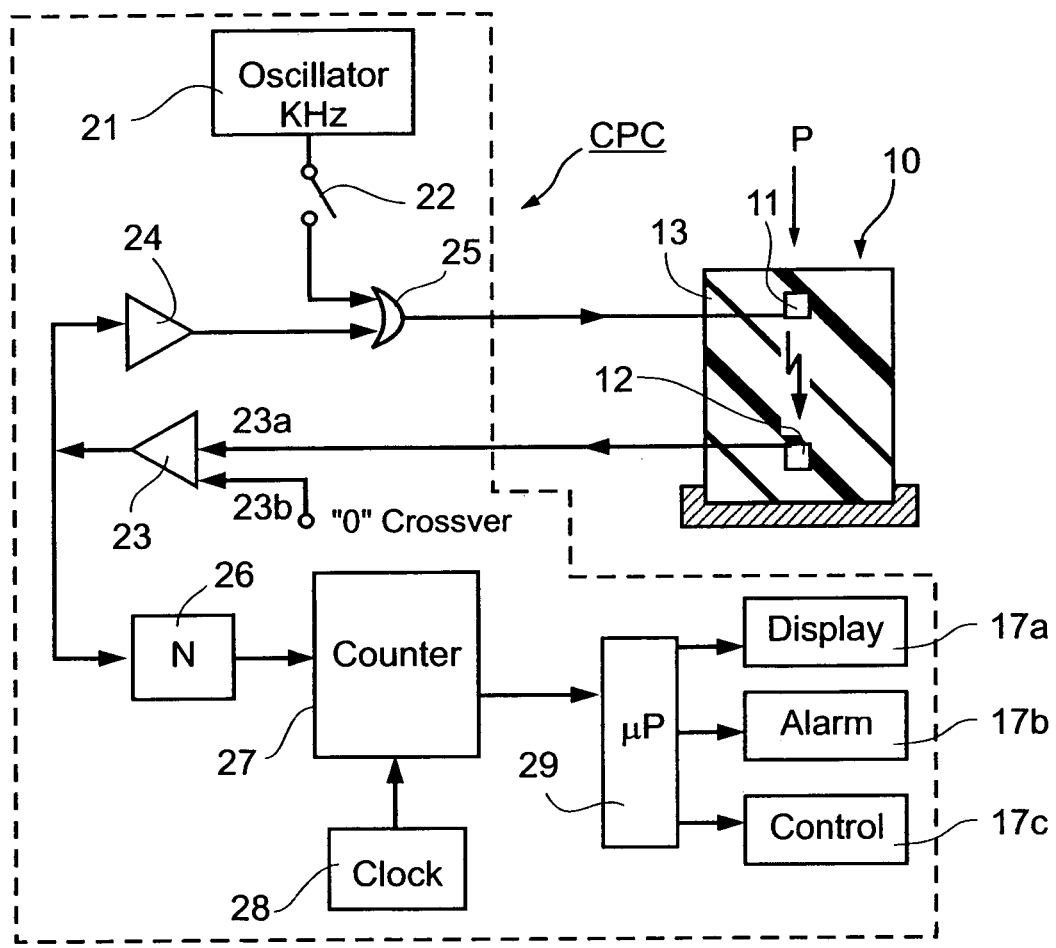
FIG. 2 is a block diagram more particularly illustrating the control and processing circuitry (CPC) in the apparatus of FIG. 1.

FIG. 2 more particularly illustrates the control and processor circuitry CPC of FIG. 1. As more particularly described in the above-cited International Patent Applications and U.S. Patent such circuitry is constructed and operates as follows:

Initially, oscillator 21 is energized while switch 22 is closed so as to cause transmitter 11 to transmit a succession of sonic pulses until such pulses are received by receiver 12. Once the pulses are received by receiver 12, switch 22 is opened so that the pulses received by receiver 12 are thereafter used for controlling the transmitter 11.

As shown in FIG. 2, the sonic signals received by receiver 11 are fed to a comparator 23 via its input 23a. Comparator 23 includes a second input 23b connected to a predetermined bias so as to detect a predetermined fiducial or reference point in the received signal. In the example illustrated in FIG. 2, this predetermined fiducial point is the "zero" cross-over point of the received signal; therefore, input 23b of comparator 23 is at a zero bias.

The output of comparator 23 is fed to an amplifier 24, e.g., a monostable oscillator, which is triggered to produce an output signal at each fiducial point (zero cross-over point) in the signals received by receiver 12. The outputs from amplifier 24 are fed via an OR-gate 25 to trigger the transmitter 11 for the next sonic pulse. Since switch 22 is open, transmitter 11 will thus be triggered by each signal received by the receiver 12 to transmit the next sonic pulse in the succession of pulses.

It will thus be seen that the frequency of the output pulses or signals from transmitter 12 will change with a change in the spacing between the transmitter 11 and receiver 12. It will also be seen that the number of wavelengths or pulses in the signal transmitted by transmitter 11 and received by receiver 12 will be a whole integer. This change in frequency by the transmitter 11, while maintaining the number of waves between the transmitter and receiver 12 as a whole integer, enables a precise determination to be made of the distance between the transmitter and receiver. The summing circuitry, including counter 26, counter 27, clock 28 and microprocessor 29, enables the detected frequency difference, and thereby the measurement precision, to be increased by a factor "N", such that the precision of the measurement can be preset, almost without limitation, by the selection of the appropriate frequency, clock rate for clock 28, and summation factor "N" for counter 27.

As further shown in FIG. 2, the output from microprocessor 29 of the control and processor circuit CPC may be used for display, alarm and/or control purposes, as schematically shown at 17a, 17b and 17c.

Further details of the construction and operation of such an apparatus are available from the above-cited International Applications and U.S. Pat. No. 6,621,278, incorporated herein by reference. For example, U.S. Pat. No. 6,621,278 includes a modulation feature, and also a delay line feature, which significantly extend the possible applications of such apparatus for measuring various types of parameters.

Specific implementations of the method and apparatus described in the above-cited International Applications and U.S. Patent, utilized sensors in the form of deformable membranes, bellows, spring-mounted members, or displaceable plungers. However, it has now been found that utilizing a sensor of the above-described construction illustrated at 10 in FIGS. 1 and 2, namely one including a body of soft elastomeric material 13, preferably embedding the transmitter 11 and receiver 12 in spaced relation to each other, enables considerably higher sensitivity to be attained of the displacement being detected and measured.

It will thus be seen that the body of soft elastomeric material 13 between the transmitter 11 and receiver 12 defines an acoustical channel between the transmitter and receiver. It will also be seen that the pressure P applied to the sensor changes the effective length of this acoustical channel such that, measuring the instantaneous length of the channel by measuring the transit time of a sonic pulse from the transmitter to the receiver, produces a measurement of the pressure applied to the sensor. The sensor of FIGS. 1 and 2, therefore, is a displaceable-type pressure sensor in which a measurement of the displacement, or change in effective length, of the acoustical channel produces a measurement of the pressure applied to the sensor. The circuit illustrated in FIG. 2 detects displacement with particularly high sensitivity, enabling a measurement of particularly high accuracy to be made of the force P applied to the sensor.

It will be appreciated that the displacement-type sensor illustrated in FIGS. 1 and 2 can also be used for producing highly accurate measurements of other parameters which change the effective length of the acoustical channel defined by the soft elastomeric material 13 between the transmitter 11 and receiver 12. Examples of other parameters include torque, centrifugal force, respiratory pulsations, blood pressure pulsations, weight, etc., as will be described more particularly below.

As will also be described more particularly below, the sensor could include a weight acting as an inertia member to produce an acceleration-type sensor in which changes in the displacement are detected and used for producing a measurement of the respective parameter. Such acceleration-type sensors are particularly useful where the displacements occur frequently or rapidly.

Preferred materials for the elastomeric body 13 in FIGS. 1 and 2 are silicone rubber compounds, e.g., those supplied by Smooth-on Ltd. under the Trademark "Dragon Skin" and "Dragon Skin Q"; those supplied by Rhodia, Inc. of Cranbury, N.J. under the Trademark "Rhodorsil" RTV-585; and RTV Silicone rubber compounds supplied by General Electric Company. Preferably, the elastomeric material should have a Shore A hardness of 5-60, and more preferably from 7-20. For many of the applications described below, a Shore A hardness of 10 was found to produce best results.

Such materials have high sonic-wave transmissivity properties and low sonic-wave attenuation properties. They are also characterized by a Young's modulus of elasticity $10^5$ times lower than steel, and a Poisson's ratio of almost 0.5. These properties have been found to produce the exceptional and unexpected sensitivity to detecting displacements attainable by sensors constructed according to the present invention.

The frequency of oscillator 21 would depend, to a large extent, on the particular application of the sensor. In most of the applications described below, the frequency of oscillator 21 would preferably be in the range of 500-2000 kHz, preferably about 700 kHz.

FIGS. 3-39 illustrate examples of a number of constructions and applications of displacement-type and acceleration-type sensors for use in the apparatus of FIGS. 1 and 2.

Figure 3:
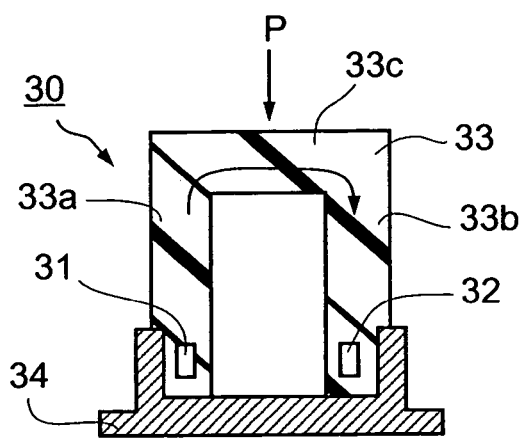
FIG. 3 illustrates another sensor construction in accordance with the present invention.

Thus, FIG. 3 illustrates a displacement-type sensor, therein generally designated 30, which also includes a sonic transmitter 31 and a sonic receiver 32 embedded in an elastomeric body 33 mounted on a mounting member 34 at the opposite face of body 33 to receive the pressure P being measured. In this case, the elastomeric body 33 is formed with a first leg 33a in which the transmitter 31 is embedded, and a second leg 33b in which the receiver is embedded, such that the receiver receives the sonic pulses from the transmitter 31 via a bridge 33c bridging the two legs. Such an arrangement thus provides an acoustical channel of compact construction having a relatively long sonic-wave transmission path between the transmitter and receiver.

Figure 4:
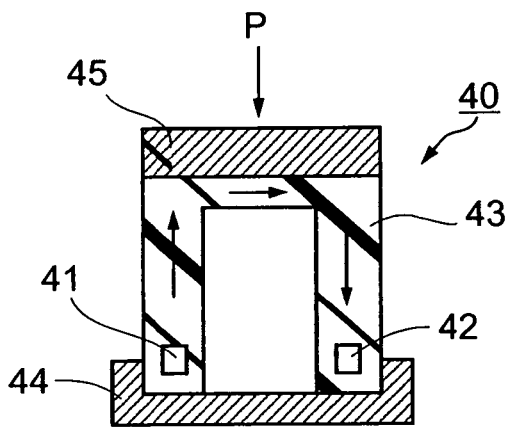
FIG. 4 illustrates an acceleration-type sensor construction in accordance with the present invention.

FIG. 4 illustrates an acceleration-type sensor, therein generally designated 40, of a similar construction as in FIG. 3, to include a transmitter 41 embedded in one leg of an elastomeric body 43, a receiver 42 embedded in another leg and communicating with the transmitter via a bridge, and a mounting member 44 for mounting the elastomeric body 43. In this case, however, the bridge end of the elastomeric body 43 carries a weight 45, which acts as an inertia member, to produce the force to be applied to the elastomeric body upon its displacement. Sensor 40 may thus be used as an accelerometer for measuring linear acceleration of a body. As will be described below, such a sensor may also be used to measure changes in the angular or rotational velocity of a body by sensing changes in the centrifugal force generated by the weight during the rotation of the body.

FIG. 5 illustrates an example of an application of a sensor, therein generally designated 50, for application to the chest of a person in order to measure or detect the respiration or cardiac rate of the person. For such application, the elastomeric body, therein designated 53, containing the transmitter 51 and receiver 52 embedded therein at spaced locations, would be secured, e.g., by an elastic band 55, to the chest of the patient, while applying a predetermined pressure thereto, such that the changes in the locations between the transmitter and receiver, produced by the pulsatile movements of the chest, will provide a measurement of the respiration rate and/or cardiac rate of the individual.

Sensor 50 illustrated in FIG. 5 may be of the accelerometer type as illustrated in FIG. 4, or the displacement-type of FIG. 3, as well as of other constructions described below.

FIG. 6 illustrates a sensor, therein generally designated 60, which may be of the same construction as in FIG. 5, except that it is to be applied to the wrist of the individual, and therefore includes a wrist-band 65, for purposes of detecting and measuring the individual's pulse. Sensor 60 illustrated in FIG. 6 may also be of the accelerometer type or of the displacement-type as described above with respect to FIG. 5.

FIG. 7 illustrates a sensor 70 of similar construction as in FIGS. 1 and 2, to include a transmitter 71 and receiver 72 embedded in spaced relationship within the elastomeric body 73. In this case, one side of body 73 carries a printed circuit board 74 which includes at least part of the control and processor circuitry CPC of FIGS. 1 and 2. The other side of elastomeric body 73 may carry another printed circuit board 75 including the remainder circuitry and/or a weight to enable the sensor to serve as an accelerometer, as in FIG. 4.

FIG. 8 illustrates a sensor 80 constructed in accordance with the present invention to serve as a finger probe for sensing pulsatile blood flow in a person's finger and the temperature of the finger. For this purpose, sensor 80 includes an elastomeric body 83 having a transmitter 81 and receiver 82 embedded therein in spaced relation, as described above, to produce an output for measuring displacement, as shown at 84.

In this case, however, elastomeric body 83 includes a second sonic transmitter 85 and second sonic receiver 86 spaced therefrom but bridged by a path 87 of a temperature-sensitive material (e.g., metal) exposed to the temperature of the finger. Since the velocity of the sonic waves between transmitter 85 and receiver 86 is changed by a change in temperature of the metal path 87, the control and processor circuitry CPC (FIGS.

1, 2) will produce an output of the measured temperature, as shown at 88, as described more particularly in the above-cited International Applications. This temperature measurement can be outputted to a display for viewing, and/or can be used for providing temperature compensation of the displacement measurement 84, as schematically shown by block 89 in FIG. 8.

It will thus be seen that the device illustrated in FIG. 8 actually includes two sensors each having its own acoustical channel for sensing a predetermined parameter. Thus, the soft elastomeric material 83 between transmitter 81 and receiver 82 defines one acoustical channel which senses displacement; whereas the temperature-sensitive path 87 between transmitter 85 and receiver 86 defines a second acoustical channel which senses temperature. Both channels produce a change in the transit time of a sonic wave from the transmitter to the receiver of the respective channel in accordance with the parameter being sensed. Thus, the acoustical channel between transmitter 81 and receiver 82 defined by the soft elastomeric material 83 between them changes its effective length in response to the parameter (pressure) to be measured, whereas the acoustical channel between transmitter 85 and receiver 86 changes its sonic-wave transmissivity in response to the measured parameter (temperature).

Figure 9C:

FIGS. 9a-9c illustrate the apparatus of the present invention used for monitoring a condition of an individual in a bed. It has been found that the extremely high sensitivity of the measuring apparatus enables detection, not only of movements, breathing or cessation of breathing (apnea), but also heart activity of the individual.

Thus, as shown in FIG. 9a, a sensor (90a-90c) is inserted under each of the four legs of the bed BD. As shown in FIG. 9b, each sensor is of a construction as described above, to include a transmitter 91 and a receiver 92 embedded in spaced relationship to each other in a body 93 of elastomeric material mounted on a flat mounting member 94. Where a leg of the bed is mounted on a wheel or roller, as shown at 95, the upper end of the sensor 90 is provided with a cap 96 shaped to accommodate the roller or wheel 95. FIG. 9c schematically illustrates the electrical circuitry connecting the four sensors 90a-90d in series to produce an output to the control and processor circuit 98.

It will thus be seen that the arrangement illustrated in FIGS. 9a-9c enables detecting the vital signs (respiration, cardiac activity), as well as movements, of the occupant of the bed. Instead of connecting the outputs of the sensors in series for integration as in FIG. 9c, the outputs could also be connected in parallel, where each output signal is independent from the others. A preferred alternative would be to have the feedback from the receiver to the transmitter to pass along the full loop of several sensors so that the resulting frequency depends on the total delay in all the sensors, that is, the receiver of one sensor would trigger the transmitter of the next sensor in the loop, such that the system requires only one measurement channel. Also, only one or two sensors could be used. The wires used to connect the sensors can be attached to the bed frame. The sensors can be made waterproof and can be designed of such high sensitivity so as to be capable of sensing very small movements or vibrations involving forces of a few grams.

Figure 10:
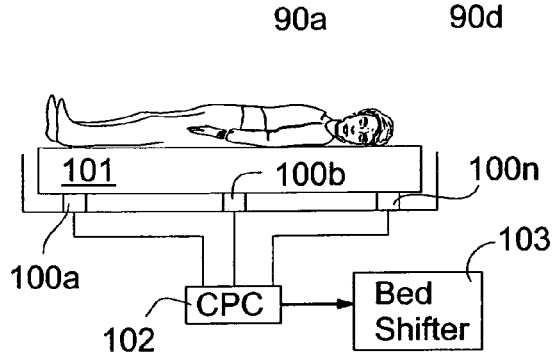
FIG. 10 illustrates an application of the invention for use to prevent bedsores.

FIG. 10 illustrates the sensor of the invention applied to prevent bedsores. For this purpose, a plurality of sensors 100a, 100b-100n, may be located, in any desired number and pattern, under a mattress 101 to sense a particular area of the individual's body in contact with the mattress for any movement, changes in blood flow, etc. All the sensors are connected to a control and processor circuitry 102 effective, if no movement is detected, or if the blood flow rate drops in a predetermined area within a predetermined time period, to actuate a bed shifter 103 in order to shift the mattress or the bed such as to cause a change in the position of the individual, and thereby to reduce or eliminate the chances of producing bedsores.

It has been found that sensors constructed in accordance with the present invention enable such a high degree of sensitivity to be obtained that they can be located under the mattress 101, within the mattress, or on the upper surface of the mattress so as to be in direct contact with the individual's body.

While FIG. 10 illustrates the system as applied to a mattress for avoiding bedsores, the same system can be included in the seat pad of a wheelchair. Also, while the device controlled is a shifting device for a bed, mattress, or pad shifter, a massaging or pulsating device could be controlled to massage or pulsate the affected area. In addition, they can serve as apnea monitors; and where the bed is a double bed to be occupied by two persons, two such sensors may be used, one on each side, connected to a common alarm to be actuated if a monitored emergency condition (i.e., a respiration or cardiac condition) is detected with respect to either bed occupant.

Figure 11:
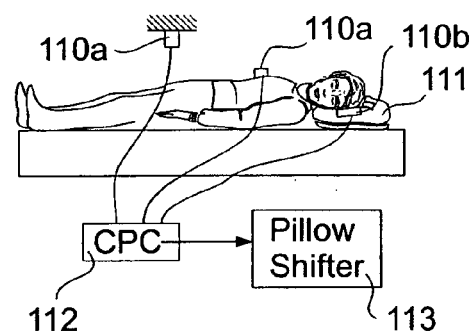
FIG. 11 illustrates an anti-snoring application of the invention.

FIG. 11 illustrates an application of the invention as an anti-snoring device. When so used, one or more of the sensors, shown at 110a-110n, preferably of the acceleration-type, may be applied to the chest, bed, stand, and/or pillow of the individual to produce outputs to the control and processor circuitry 112. The latter circuit would be programmed to recognize outputs indicating a "snoring" occurrence and automatically to actuate a pillow shifter 113 to shift the pillow, or to produce another disturbance (e.g., a gentle "poke") to the individual in an attempt to interrupt the snoring. The arrangement illustrated in FIG. 11 thus provides a biofeedback system in which the user is disturbed each time snoring is detected, with the object of slowly decreasing to zero the amount of snoring.

Figure 12:
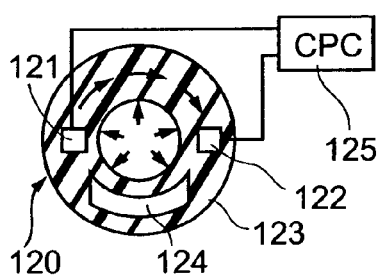
FIGS. 12-14 illustrate various constructions of sensors in accordance with the present invention for monitoring pulse rate.
Figure 13:
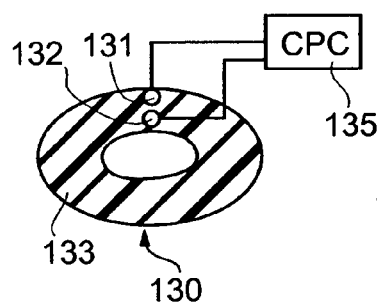
Figure 14:
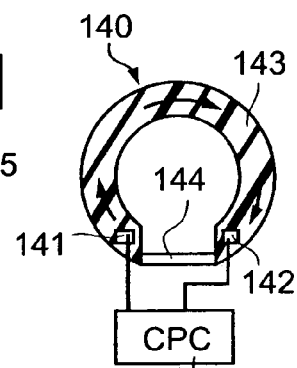

FIGS. 12-14 illustrate the invention applied to various types of finger probes for measuring pulse rate, blood pressure, or other cardiovascular condition of the individual.

In FIG. 12, the sensor, therein designated 120, is of ring shape to be received on a finger of the individual. It includes a transmitter 121 and a receiver 122 embedded within a body of elastomeric material 123 of annular configuration. The body 123 is formed on one side with an air cavity 124, to thereby define an acoustical channel on the other side for the sonic pulses from the transmitter 121 to the receiver 122. As schematically shown in FIG. 12, transmitter 121 and receiver 122 are connected to a control and processor circuit 125 which produces a measurement of the changes in the length of the sonic path resulting from the pulsatile blood flow through the finger.

FIG. 13 illustrates a similar sensor 130 as in FIG. 12, except that the transmitter 131 and receiver 132 are located in radial alignment on one side of the elastomeric body 133 to produce a radially-extending acoustical channel, and the elastomeric body is of elliptical shape so as to apply a compressive, but non-occluding, force to the finger received within the opening of the sensor. As described above, the pulsatile blood flow through the individual's finger will be sensed by the change in relative position between the transmitter 131 and receiver 132, to produce a measurement of the pulse rate.

FIG. 14 illustrates a finger-probe type sensor 140, similar to that of FIGS. 12 and 13, including a transmitter 141 and receiver 142 embedded at spaced locations within an elastomeric body 143 of ring-shape. In this case, however, the ring is closed by a band 144, which applies a predetermined compressive force to the finger received within the ring. The presence of band 144 also causes the sonic pulses to be directed through the desired acoustical path from the transmitter 141 to the receiver 142.

Figure 15:
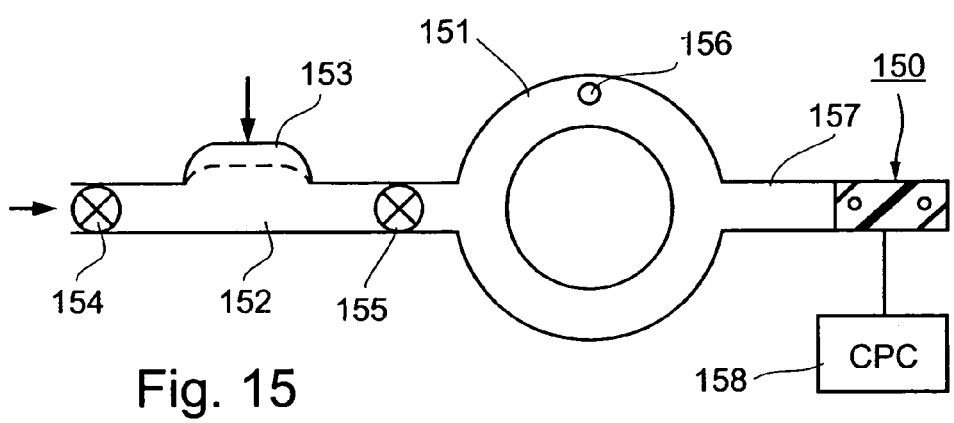
FIG. 15 illustrates an application of the invention for non-invasively measuring blood pressure according to the oscillometric method.

FIG. 15 illustrates a sensor, therein designated 150, used in a system for measuring blood-pressure according to the oscillometric method. The system illustrated in FIG. 15 includes a cuff 151 inflatable via a tube 152 by a manual pump 153 and a one-way valve 154. Tube 152 further includes a valve 155 which automatically closes when the cuff has been inflated to the desired pressure. When so inflated, the pressure within the cuff 151 is gradually decreased by a small hole 156 formed in the cuff.

The pressure within the cuff is continuously monitored by sensor 150 connected to the cuff by means of a tube 157. Sensor 150 is electrically connected to the control and processing circuit 158 to control the sensor in the manner described above, and also to output the cuff pressure measurements as sensed by the sensor.

Cuff 151 is preferably dimensioned so as to be received on a finger of the subject, and thus to sense the arterial blood flow through the finger. It will be appreciated, however, that cuff 151 could also be dimensioned to enclose an arm of the person, as in the conventional oscillometric method of measuring blood pressure.

According to this method of blood pressure measurement, cuff 151 is inflated by pump 153 to a pressure above the patient's systolic pressure, whereupon valve 155 automatically closes. The small hole 156 in cuff 151 (or in connecting tube 157) gradually reduces the pressure within the cuff. Pressure sensor 150, controlled by the control and processing circuitry 158, continuously measures the pressure within the cuff and produces outputs of such measurements.

According to this technique of blood pressure measurement, the pressure fluctuations within the patient's artery resulting from the beats of the patient's pulse are transferred to the inflated cuff 151, causing slight pressure variations within the cuff as the cuff is gradually deflated. Thus, the output from the pressure sensor 150, as appearing in its control and processing circuitry 158, would generally be a DC component representing the decreasing cuff pressure, and a serious of small periodic variations associated with the beats of the patient's pulse. These small variations are often referred to as "oscillation complexes", or simply "oscillations". A patient's blood pressure may be estimated in accordance with the known oscillometric method of blood pressure measurement based on an analysis of these oscillation complexes.

Because of the exceptionally high sensitivity to displacements attainable by sensor 150 constructed in accordance with the present invention, such a sensor is particularly useful for this method of blood pressure measurement.

Figure 16:
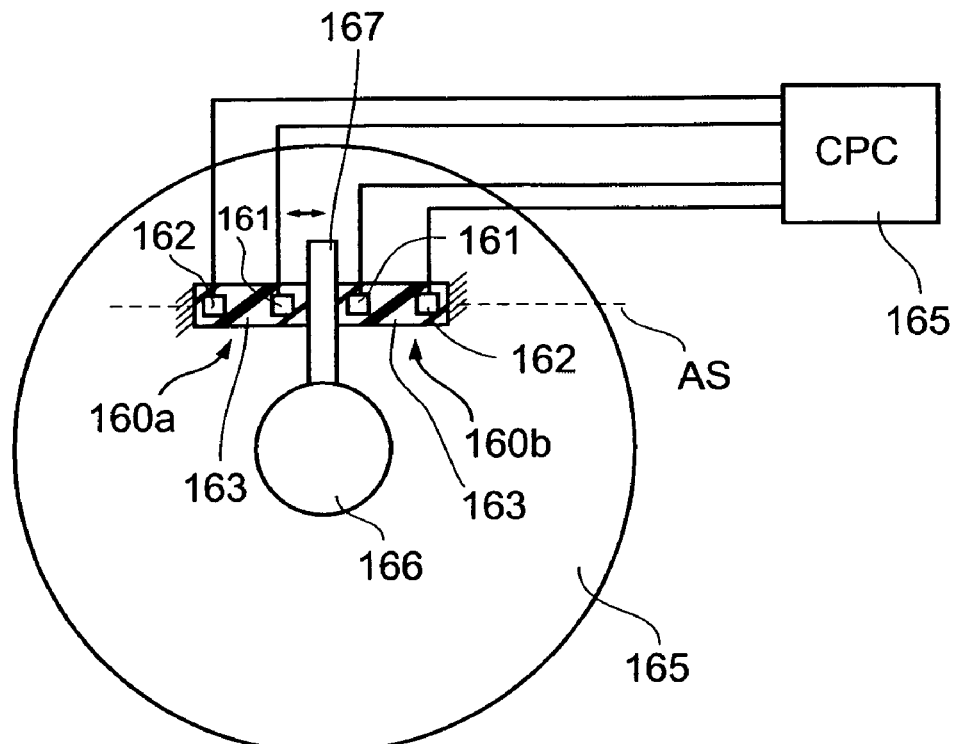
FIG. 16 illustrates an application of the invention for measuring torque in a transmission system, e.g., in a vehicle.

FIG. 16 illustrates the application of the invention for measuring torque, e.g., in a drive shaft of a motor vehicle transmission system. It also illustrates another feature of the present invention, namely for eliminating or reducing the effects of temperature drifts (or other transient effects) in the measurements.

The apparatus illustrated in FIG. 16 includes two sensors 160a, 160b, each of the same construction as described above to include a transmitter 161 and a receiver 162 embedded within a body of elastomeric material 163 defining an acoustical channel. The two sensors 160a, 160b are fixed at one of their ends to the flywheel 165 of the vehicle transmission system, with the opposite ends facing and aligned with each other.

The drive shaft 166 of the vehicle drive system is provided with an arm 167 which is located between, and secured to, the facing ends of the two sensors 160a, 160b. The two sensors are connected to the control and processor circuitry 165 in a subtractive manner, such that the output frequency of one sensor will be subtracted from that of the other sensor.

Assuming the drive shaft 166 is rotating in the direction of the arrow (clockwise), it will be seen that an increase in the torque applied to the drive shaft will compress sensor 160a, and will expand sensor 160b. Thus, the output frequency of sensor 160a will be increased (+Δf) while the output of sensor 160b will be decreased (−Δf). On the other hand, the temperature drift ($\Delta f_T$), velocity, or other transient influences, will be the same with respect to both sensors. Accordingly, by subtracting the output of sensor 160b from that of sensor 160a, there is produced an output torque (T) which is a function of 2Δf, since the temperature drift component of each frequency is cancelled from the other. Thus:

$$T = f_1 - f_2 = (f_0 + \Delta f + \Delta f_T) - (f_0 - \Delta f + \Delta f_T) = 2\Delta f$$

The arrangement illustrated in FIG. 16 thus, not only eliminates or reduces the effects of temperature drift (as well as other transient influences), but also significantly increases the output signal. In addition, since the forces applied to the two sensors along any axis, other than the axis AS as illustrated in FIG. 16, will have a similar influence on the output frequencies of the two sensors as the temperature drift influence, those forces (such as centrifugal forces due to velocity variations) will also tend to cancel out when the output frequency of one sensor is subtracted from the other, such that axis AS in FIG. 16 will be substantially the only axis of sensitivity.

It will be appreciated that the foregoing features in the application illustrated in FIG. 16, which enhance the accuracy of the measurements, may also be used in the many other applications, such as those previously described or to be described below.

Figure 17:
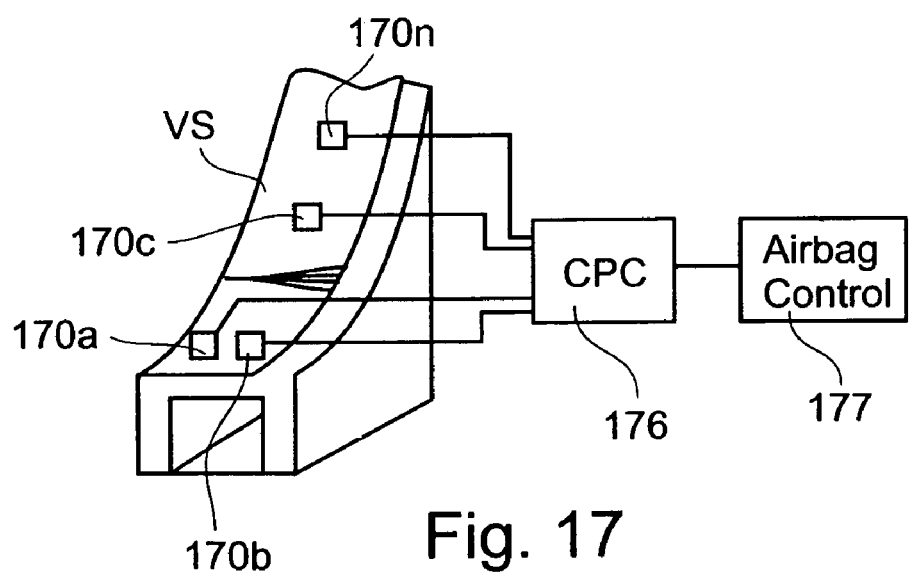
FIG. 17 illustrates an application of the invention for monitoring a vehicle seat, e.g., in order to detect the presence, weight, respiration activity, cardiac activity, etc., of an occupant, e.g., to control an air bag.

FIG. 17 illustrates a further application of the invention applied to a vehicle seat, e.g., for monitoring the condition of the occupant of the seat, and/or for controlling an airbag in accordance with the presence or absence of an occupant, or the weight of the occupant (e.g., to distinguish a child from an adult). Thus, FIG. 17 illustrates a vehicle seat VS including one or more of the sensors 170a-170n carried at various locations thereon, according to the particular application. FIG. 17 further illustrates the control and processor circuitry 176 for controlling the various sensors and for producing the desired outputs, e.g., as described above with respect to FIGS. 1 and 2, but further including an air bag actuator 177, if the outputs are intended to control the actuation of the air bag. For example, the air bag could be controlled so as to be actuated only when breathing or a blood pulse has been detected from the respective vehicle seat to indicate the seat is occupied. The detected respiration and/or blood pulse rate could also be detected, together with the weight of the occupant, e.g., to distinguish a child from a small adult, and to control the air bag actuation accordingly.

Figure 18A:
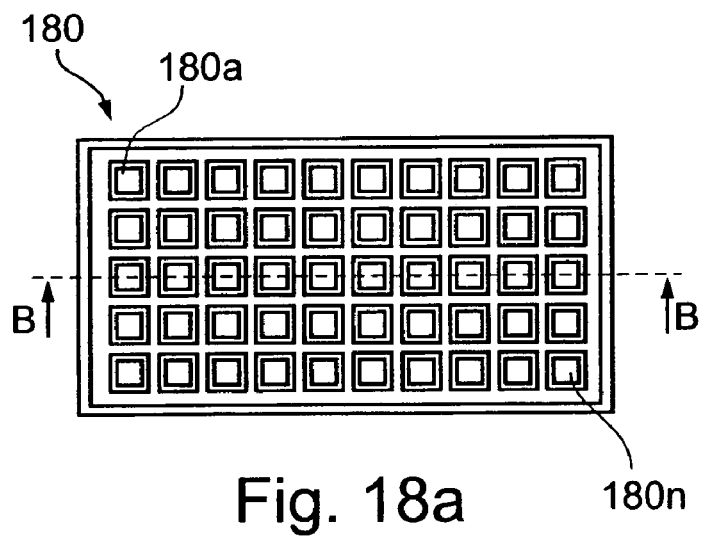
FIGS. 18a-18c illustrate the invention embodied in a matrix of sensors for use as a keyboard or as a pressure distribution sensor.
Figure 18B:
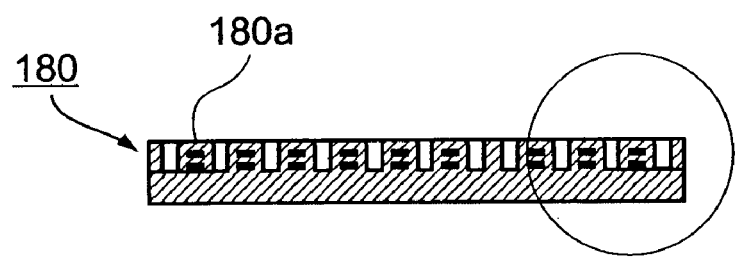
Figure 18C:
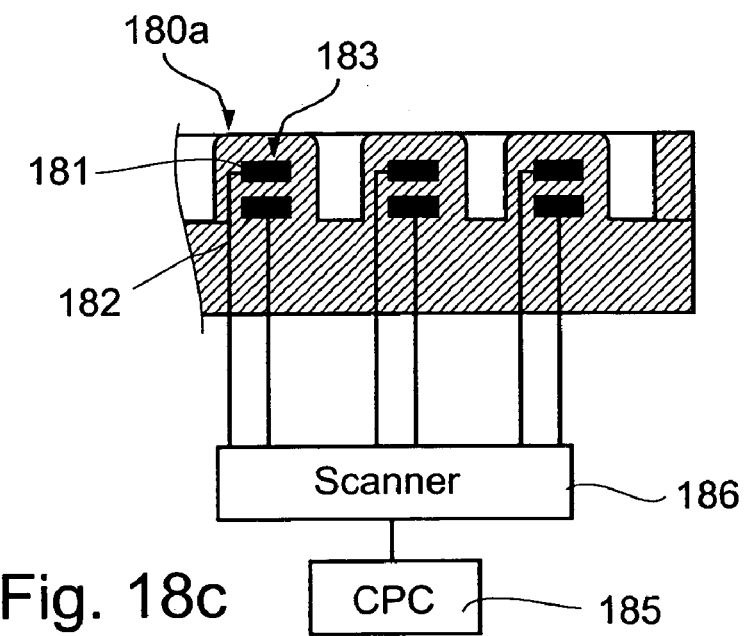

FIGS. 18a-18c illustrate a sensor assembly, generally designated 180, including a plurality of sensors 180a-180n arranged in a matrix, with each sensor including a sonic transmitter 181 and a sonic receiver 182 embedded in spaced relationship within an elastomeric body 183. Elastomeric body 183 may be common for all the sensors 180a-180n, or may be a separate body for each such sensor. All the transmitters and receivers are connected to a common control and processing circuit 185 via a scanner 186 which sequentially scans the sensors in order to control them and to receive their outputs.

Such a sensor assembly as illustrated in FIGS. 18a-18c may thus be used in several of the foregoing applications, e.g., to detect vital signs in the bed or wheelchair application of FIGS. 9a-9c, to prevent bed sores in the application of FIG. 10, or to sense weight, respiration, and/or cardiac rate in an air bag control apparatus of FIG. 17. Since the operating elements of the assembly are all embedded within a plastic (the elastomeric material), such a sensor assembly could also be used as a water-proof keyboard or other input device. The water-proof property of the sensor assembly also enables it to be used, in single-sensor units or multiple-sensor units, as electrical switches or other input devices for controlling various types of appliances, such as washing machines, water heaters, or the like, that may involve a danger when exposed to water.

FIG. 19 illustrates a sensor 190 according to any of the above constructions used for measuring the pressure within a pressurized container 195. FIG. 20 illustrates such a sensor 200 used for measuring the pressure within a pressurized pipe 205.

FIG. 21 illustrates sensor assemblies 210 constructed as described above for supporting a scale 215 in order to measure the weight of an object placed on the scale. In the example illustrated in FIG. 21, the scale 215 is supported in suspension at each of its four corners by an assembly of two sensors 210a, 210b, arranged in a differential or subtractive relationship as described above with respect to FIG. 16 in order to compensate for temperature.

FIG. 22 illustrates a sensor, therein designated 220, used for measuring the density of a liquid 225 in which the sensor is immersed. For example, the liquid could be water within a swimming pool 226 wherein the measured density would indicate the concentration of chlorine in, or the pH of, the water. Preferably, sensor 220 illustrated in FIG. 22 also includes a temperature-sensitive sensor element 227, as described above with respect to FIG. 8, e.g., for providing temperature compensation for the measurement outputted by sensor 220. Sensor 220 can also be used as a depth gauge for measuring the depth in which it is immersed in a body of water or other liquid.

FIG. 23 illustrates a sensor constructed in accordance with the present invention for measuring the intensity of a magnetic field. Such a sensor, generally designated 230, could be any of the above-described constructions, to include a sonic transmitter 231 and a sonic receiver 232 embedded in spaced relationship to each other in a body of elastomeric material 233 defining the acoustical channel of the sensor. In this case, however, one or both ends of the body of elastomeric material would carry a magnet, as shown at 234, such as to produce a force compressing or expanding the acoustical channel in accordance with the magnetic field sensed by the sensor.

FIG. 24 illustrates an assembly including two acceleration-type sensors 240a, 240b mounted on a body 241 rotatable about a rotary axis 242. Both sensors 240a, 240b include a weight 245a, 245b, respectively, as described above with respect to FIG. 4. In this case, however, sensor 240a is carried by rotary body 241 such that its weight 245a is located radially outwardly; therefore sensor 240a would provide a measurement of the centrifugal force produced by the weight, and thereby a measurement of the rotational velocity of body 241. On the other hand, sensor 240b is oriented such that its weight 245d extends tangentially with respect to that sensor, and therefore its output would be a measurement of the linear velocity of rotary body 241.

FIG. 25 illustrates a sensor, generally designated 250, constructed in accordance with the present invention for measuring the linear velocity of an object in a fluid medium, e.g., for measuring the speed of an aircraft through air, based on the Pitot tube measurement technique. The Pitot tube is oriented in the direction of travel. It includes a pair of chambers 251, 252 at one end of the Pitot tube, a main passageway 253 oriented in the direction of travel of the vehicle and communicating with chamber 251, and a plurality of openings 254 oriented perpendicularly to the direction of travel of the vehicle and communicating with both chambers 251, 252.

It will thus be seen that the pressure within chamber 251 is the total pressure ($P_T$), being the sum of the dynamic pressure ($P_D$) sensed via passageway 253, and the static pressure ($P_S$) sensed via passageways 254; whereas the pressure within chamber 252 will be only the static pressure ($P_S$) sensed via passageways 254.

The total pressure within chamber 251 is measured by sensor 250a, and the static pressure within chamber 252 is measured by sensor 250b. Both sensors may be of any of the above-described constructions, to include an acoustical channel defined by a sonic transmitter and a sonic receiver embedded in spaced relation within an elastomeric body.

It will be seen that the dynamic pressure ($P_D$) produced by the velocity V can be determined by subtracting the static pressure ($P_S$) sensed by sensor 250b from the total pressure sensed ($P_T$) by sensor 250a. The so-determined dynamic pressure ($P_D$) may then be used for determining the velocity of the body according to the following known equation:

$$V^2 = \frac{2(P_T - P_S)}{r}$$

wherein $P_T$ is the pressure measured by sensor 250a; $P_S$ is the pressure measured by sensor 250b; and r is the local value of air density.

Figure 26:
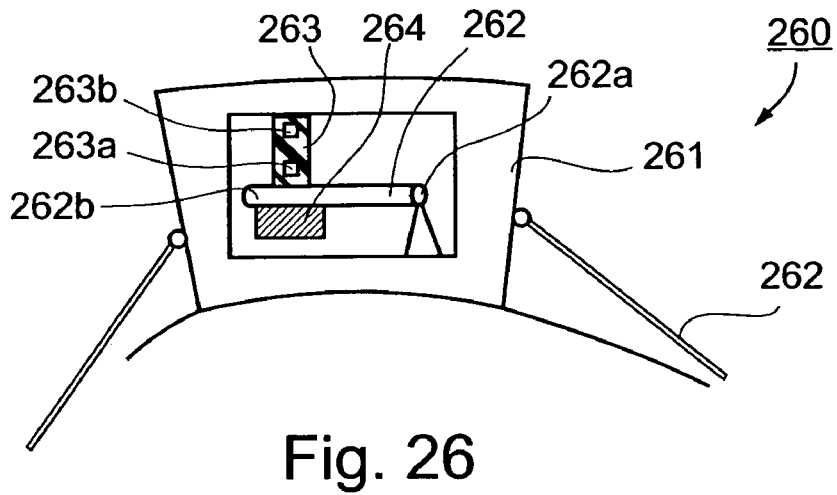
FIG. 26 illustrates the invention embodied in an acceleration-type sensor.

FIG. 26 illustrates the invention embodied in an acceleration-type sensor, generally designated 260, including a housing 261. Housing 261 serves as a mounting member for mounting the sensor to a patient's body PB, e.g., by an elastic belt 262 to detect respiration and/or cardiac activity, in the manner illustrated in FIG. 5. In this case, however, sensor 260 includes an arm 262 pivotally mounted at one end 262a to housing 261. One face of the opposite end 262b of arm 262 is secured, as by an adhesive, to one end of a body 263 of soft elastomeric material defining an acoustical channel between a sonic transmitter 263a and receiver 263b embedded therein in spaced relation to each other. The opposite end of the soft elastomeric body 263 is secured, as by an adhesive, to the inner surface of housing 261. The lower face of end 262b of pivotal arm 262 carries a weight 264, e.g., secured thereto by an adhesive.

The construction illustrated in FIG. 26 provides an extremely sensitive acceleration-type sensor which detects the respiratory and cardiac movements of the patient's body PB and produces a highly accurate measurement of such movements.

It will be appreciated that the acceleration-type sensor illustrated in FIG. 26 may be mounted to another surface of the patient's body, e.g., the wrist or arm, in order to detect and measure the displacements produced by cardiac activity, i.e., blood pulses, of the patient. Such an acceleration-type sensor may also be used in many non-medical applications, such as in seismic detectors, security fences, etc. where highly-sensitive detection or measurement of fast-action or high-frequency movements is required.

Figure 27:
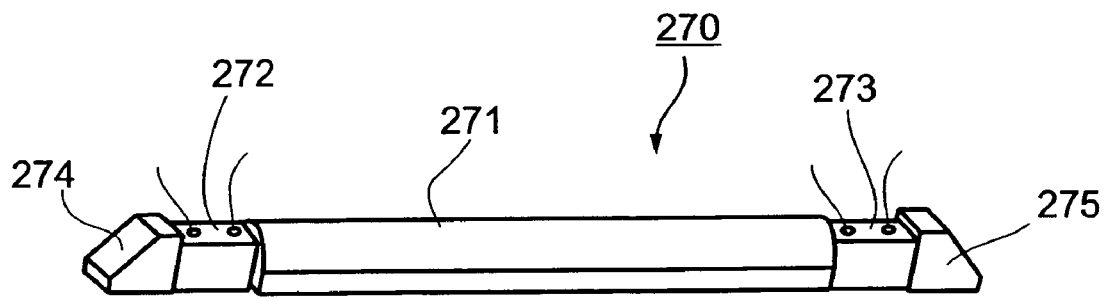
FIG. 27 illustrates a further construction of a sensor in accordance with the invention.

FIG. 27 illustrates a sensor, generally designated 270, wherein the soft elastomeric material 271 is in the form of a narrow strip such as to define a narrow acoustical channel between the spaced sonic transmitter 272 and receiver 273. The sensor illustrated in FIG. 27 further includes a damper or sound absorbing material effective to absorb sonic waves except those in the narrow acoustical channel. FIG. 27 illustrates the dampers as being pre-formed bodies 274, 275, at each of the opposite ends of the acoustical channel. A suitable material for the dampers 274, 275 is relatively soft rubber having high sonic-wave attenuation properties. While FIG. 27 illustrates the dampers applied just to the opposite ends of the acoustical channel, it will be appreciated that such damper material could be applied over additional surfaces of the acoustical channel, such as the underlying surface.

Figure 28:
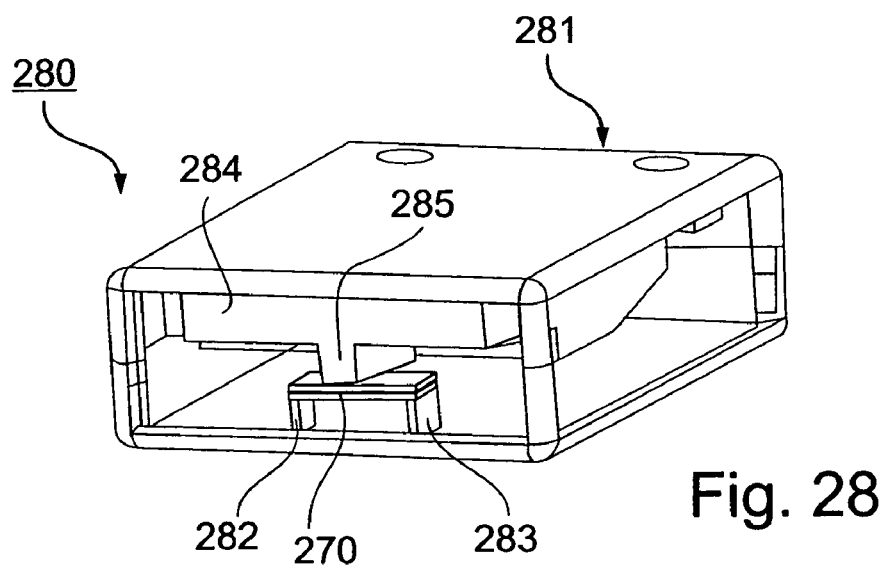
FIG. 28 illustrates the sensor of FIG. 27 implemented as an acceleration-type sensor.

FIG. 28 illustrates an acceleration-type sensor device 280 having a strip-type sensor element 270 of the construction illustrated in FIG. 27. Thus, sensor 280 includes a housing 281 mounting sensor element 270 in suspension between two posts 282, 283. Housing 281 further includes a weight 284 having a depending projection 285 at one end engageable with a mid-portion of sensor element 270. The opposite end (not shown) of weight 284 is pivotally mounted to the housing 281 such that the mid-portion of sensor element 270 is deflected by the displacement, (more particularly by the rate-of-change in the displacement) of weight 284. The acceleration-type sensor device 280 illustrated in FIG. 28 thus also provides a highly-sensitive means for detecting and/or measuring movements, and may therefore also be used in the applications described above with respect to FIG. 26.

Figure 29:
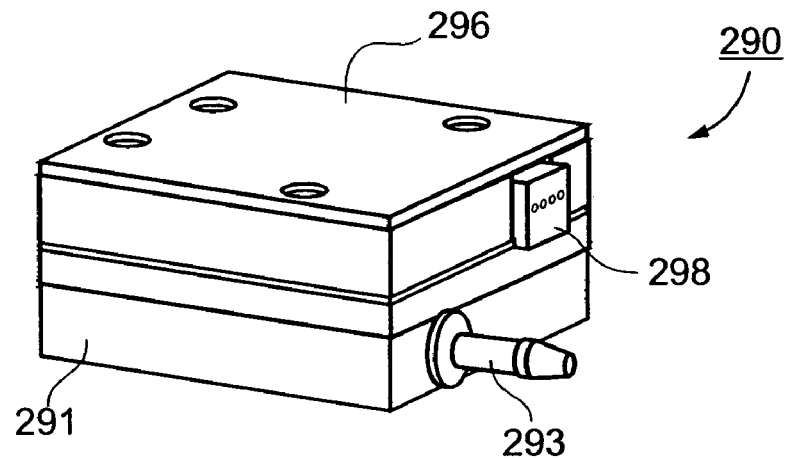
FIG. 29 is a three-dimensional view.
Figure 30:
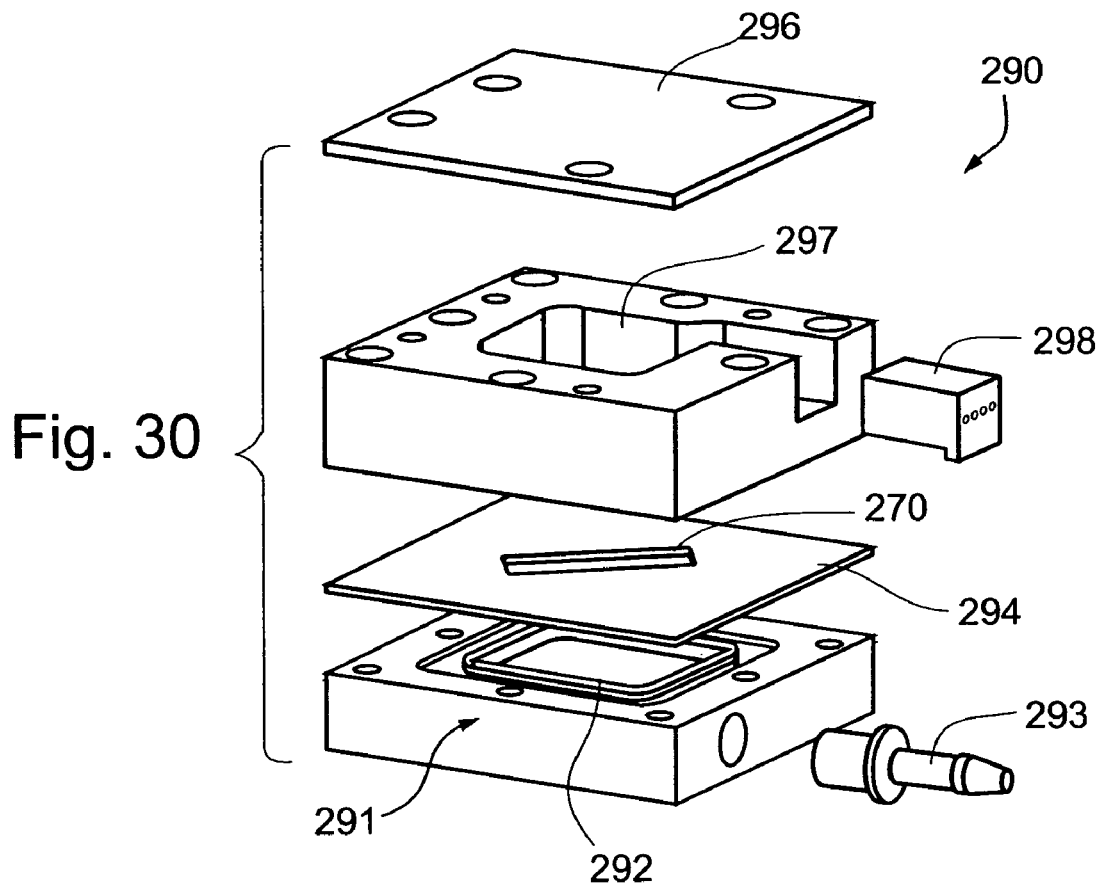
FIG. 30 is an exploded view, illustrating the sensor of FIG. 27 implemented as a pressure sensor.

FIGS. 29 and 30 are assembly and exploded views respectively, of a pressure sensor device 290 utilizing the strip-type sensor element 270 of FIG. 27 for sensing pressure in a chamber within a housing. Sensor 290 includes a housing 291 defining a chamber 292 communicating with a port 293 for a fluid whose pressure is to be measured. For this purpose, chamber 292 is closed by a membrane 293 carrying sensor element 270 of the construction described above with respect to FIG. 27 such that the membrane and the sensor element are deformable in response to the pressure within the chamber. For example, membrane 293 may be of a soft rubber having high sonic-attenuation properties so as also to act as a damper to absorb sonic waves except those in the narrow acoustical channel of sensor element 270.

Sensor device 290 further includes a block 295 and a cover 296 for securing membrane 294 over the pressure chamber 292. Block 295 is formed with a cavity 297 providing access to the transmitter and receiver of sensor element 270, and includes an electrical connector 298 for making the appropriate electrical connections to the sensor.

Figure 31:
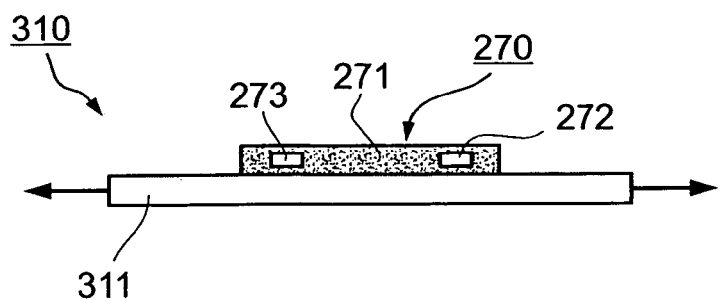
FIG. 31 illustrates the sensor of FIG. 27 embodied in an elastic belt or band sensor of extremely high sensitivity to be applied to a person for detecting respiratory or cardiac activity.

FIG. 31 illustrates a sensor device 310 particularly useful for detecting and/or measuring elongation displacements of the sensor, such as described above with respect to FIG. 5. Thus, sensor 310 includes a strip-type sensor element 270 of the construction described above with respect to FIG. 27, having a narrow acoustical channel 271 of soft elastomeric material between a sonic transmitter 272 and sonic receiver 273. In the construction illustrated in FIG. 31, sensor element 270 is mounted on an elastic member 311, such as a chest band, for detecting respiration and/or cardiac activity. Thus, the respiration and cardiac activity by the patient will produce extensions and contractions of elastic member 311 and of the soft elastomeric material 271 in the narrow acoustical channel of sensor element 270, thereby enabling the sensor to detect and/or measure such respirations or cardiac activity with a high degree of sensitivity.

Elastic member 311 of sensor element 270 is preferably of a material, such as soft rubber, having high sonic-wave attenuation properties, so as to absorb sonic waves except those in the narrow acoustical channel defined by the sensor element 270.

Figure 32:
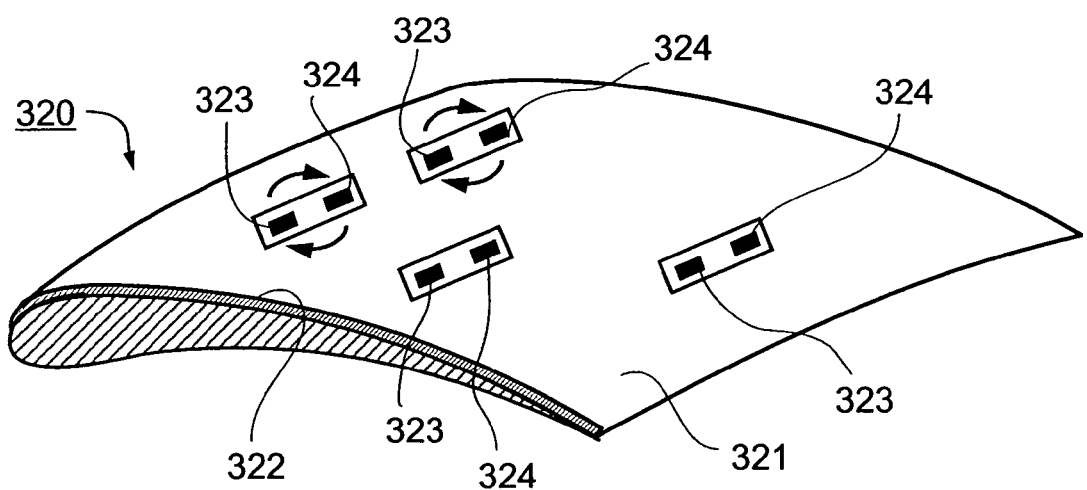
FIG. 32 illustrates the invention embodied in a sensor applied to a large surface, such as an airfoil, for detecting pressure distribution and/or deformation thereof.

FIG. 32 illustrates a sensor assembly, therein generally designated 320, for application to a surface of an object, such as an airfoil 321, to measure deformations thereof and/or pressure distribution thereon. Thus, the sensor assembly 320 includes a body of soft elastomeric material shown at 322, of a large surface area applied to, and conforming to, the surface of the airfoil 321. The soft elastomeric material body 322 includes a plurality of sonic transmitter and receiver pairs, such as shown at 323 and 324, located within the body such that each pair defines, with the portion of the soft elastic material 322 between them, a separate acoustical channel for detecting and/or measuring deformations and/or pressure distribution on the surface of the airfoil 321 occupied by the respective acoustical channel.

As an alternative arrangement, the deformations and/or pressure distribution on the surface of airfoil 320 may be detected and measured by a plurality of individual strip-type sensor elements 270, each of the construction as described above with respect to FIG. 27, fixed to the surface of the airfoil.

Figure 33:
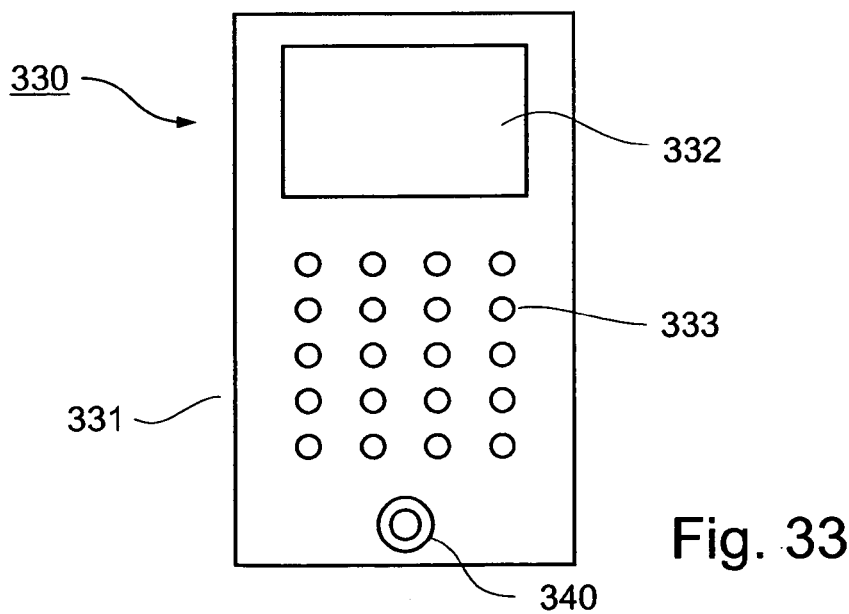
FIG. 33 illustrates the invention embodied in a cellular telephone handset or other hand-held portable electrical device.

FIG. 33 illustrates a hand-held portable electrical device, generally designated 330, such as a cellular telephone handset, PDA, or the like, incorporating a sensor 340 constructed in accordance with the present invention portable electrical device 330 may be of any conventional construction. For purposes of example, it is shown as including a casing 331 formed with a display window 332 and carrying a plurality of keys 333 for dialing a telephone number or inputting other information. Sensor 340 included in electrical device 330 is more particularly illustrated in FIGS. 34 and 35.

Figure 34:
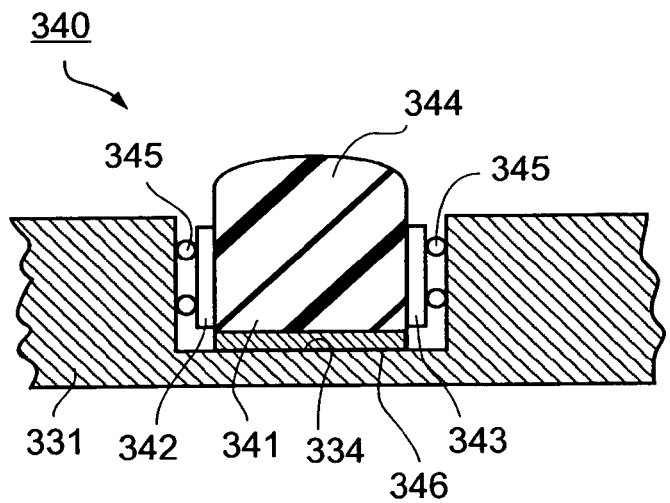
FIG. 34 is a fragmentary sectional view of a portion of FIG. 33 illustrating the sensor thereof.
Figure 35:
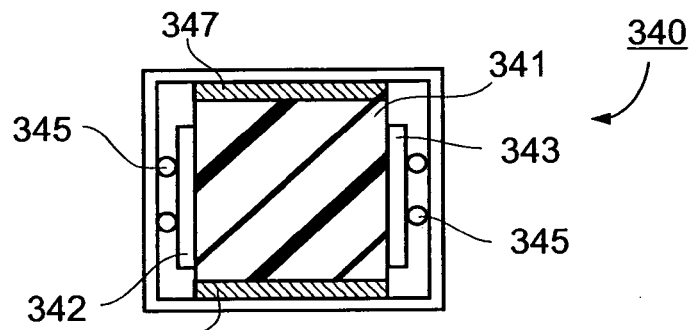
FIG. 35 is a top view of the sensor of FIG. 34.

Sensor 340 illustrated in FIGS. 34 and 35 is a displacement-type sensor. It includes a body of soft elastomeric material 341 configured as a button and received within a slot 334 formed in the housing 331. A sonic transmitter 342 and a sonic receiver 343 are fixed to the opposite sides of the soft elastomeric body 341 such that the portion of that body between the transmitter and receiver define an acoustical channel for the sonic waves transmitted by the transmitter to the receiver. The soft elastomeric material body 341 is formed with an outer convex surface 344 projecting outwardly of housing 331 so as to be engageable by a body part of the user, as will be described below. Body 341 includes deformable spacing elements 345, such as small spherical projections integrally formed on the outer surface of body 341, spacing the inner faces of the body from the sides of the housing 331, to permit expansion and contraction of the portion of body 341 between the transmitter 342 and receiver 343 when the outer face 344 of the sensor is engaged by the user's body part. The bottom of body 341, and the two sides of the body not occupied by the transmitter 342 and receiver 343, are preferably lined with sound absorbing material, as shown at 346, 347 and 348, respectively.

Sensor 340 may thus be used to detect and/or measure blood pulse rate by the user applying a finger to the outer surface 344 of the elastomeric body 341 such that the pulsations will produce changes in the effective length (compressions and expansions) of the acoustical channel between the transmitter 342 and receiver 343, thereby providing a highly sensitive detection and/or measurement of the user's blood pulse. The hand-held unit may also be used for detecting and/or measuring respiration, by pressing the outer surface 344 of the elastomeric body 341 against the user's chest, such that the respiration of the user produces the compressions and expansions of the acoustical channel between the transmitter 342 and receiver 343.

Figure 36:
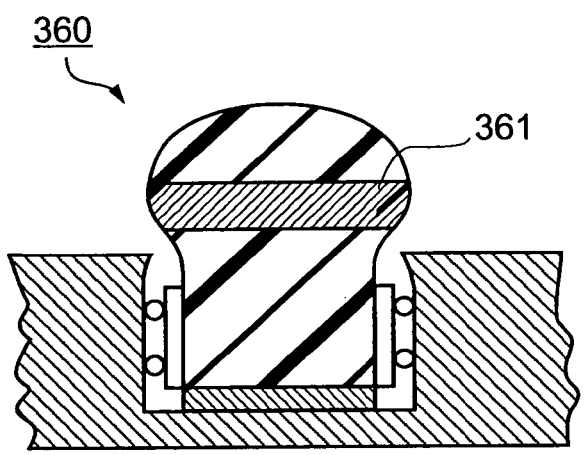
FIG. 36 is a view corresponding to that of FIG. 34 but illustrating the sensor as being of the acceleration-type to sense various types of motions, such as walking or running, as well as motions of respiratory and cardiac activity.

FIG. 36 illustrates a sensor 360 of similar construction as sensor 340 illustrated in FIGS. 34 and 35, except that it includes a weight 361, serving as an inertia member to thereby make the sensor of the acceleration-type, i.e., responsive to the rate of change of the defected displacements.

An important advantage in incorporating a displacement-type sensor (FIGS. 34, 35) or acceleration-type sensor (FIG. 36) into a cellular telephone handset is that the measurements of pulse rate, respiration rate, etc., may be transmitted, via the telephone, to remote locations for viewing, consultation, further processing, storage, or the like.

A further possible application of such a handset, particularly when including an acceleration-type sensor as illustrated in FIG. 36, is for use as a pedometer. Thus, the compression and expansion of the acoustical channel between the transmitter and receiver produced while the user is walking or running will identify the steps made by the user, and thereby provide a measurement of the number of steps traversed during any particular time period. For example, the handset could be calibrated for the distance traversed by the respective user during a walking step, and/or during a running step. Thus, by accumulating the count of running or walking steps traversed by the user, after pre-storing the length of each step, the handset could be used to provide a measurement of the total distance traversed by the user.

Figure 37:
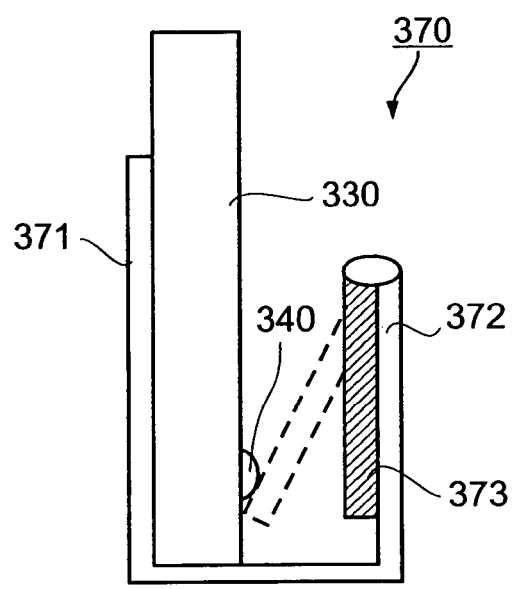
FIG. 37 illustrates the hand-held portable electrical device of FIG. 33 used as a pedometer.

FIG. 37 illustrates another arrangement, therein generally designated 370, to enable a hand-held portable electrical device, such as shown in FIGS. 33 and 34, also to be used as a pedometer for measuring traversed distances. Such an arrangement mounts the weight to a belt clip or the like holder used for carrying the device on the body of the person.

Thus, FIG. 37 illustrates a holder 371 attachable in any conventional manner to the user's belt for carrying the portable electrical device 330, with the sensor button 340 projecting outwardly towards another section 372 of the holder. Section 372 in turn pivotally mounts a weight 373 from its upper end, as shown at 374, such that each step of movement of the individual carrying the portable electrical device 330 will cause the weight 371 to pivot against sensor 340, to thereby enable that sensor to identify each step.

Figure 38:
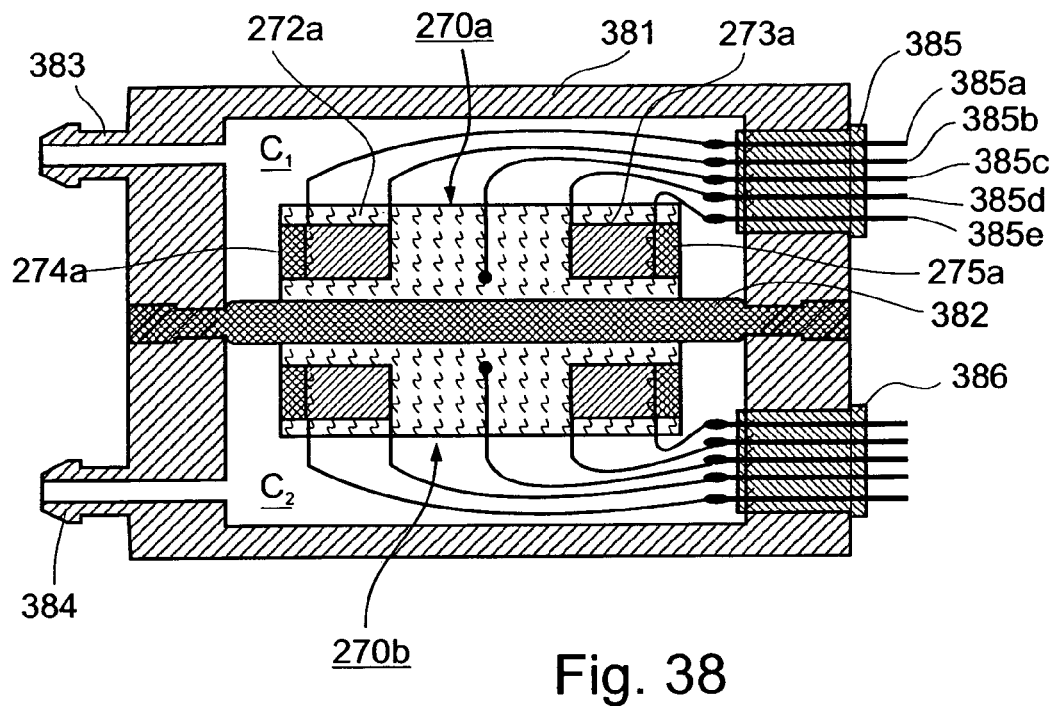
FIG. 38 is a sectional view illustrating a differential-type pressure sensor constructed in accordance with the present invention.

FIG. 38 illustrates a differential-type pressure sensor 380 constructed in accordance with the present invention. It includes a housing 381 having a deformable membrane 382 dividing the interior of the housing into two fluid chambers $C_1$, $C_2$ each having a port 383, 384, to be connected to a pressure source such that the membrane deforms in accordance with the differential pressure in the two chambers. A narrow acoustical channel of the construction illustrated in FIG. 27 is mounted on each of the opposite sides of membrane 382 so as to detect the pressure within its respective chamber according to the deformation of the membrane. Thus, one narrow acoustical channel 270a, including a transmitter 272a, receiver 273a, and the two absorber elements 274a, 275a, is mounted on one side of membrane 382; and a second narrow acoustical channel 270b, including its transmitter 272b, receiver 273b, and absorber elements 274b, 275b, is mounted on the opposite side of the membrane. Housing 381 further includes an electrical connector 385, 386, for each of the narrow acoustical channels 270a, 270b. Thus, connector 385 for acoustical channel 270a includes two terminals 385a, 385b for its transmitter 272a; two terminals 385c, 385d for its receiver 273a; and a fifth terminal 385e for a shielding electrode provided for the respective acoustical channel. Connector 386 includes corresponding terminals for the elements in its acoustical channel 270b.

It will be seen that the differential pressure in the two chambers $C_1$, $C_2$ on opposite sides of membrane 382 will produce a corresponding deformation in the membrane, which deformation will be measured by the two acoustical channels 270a, 270b.

Figure 39:
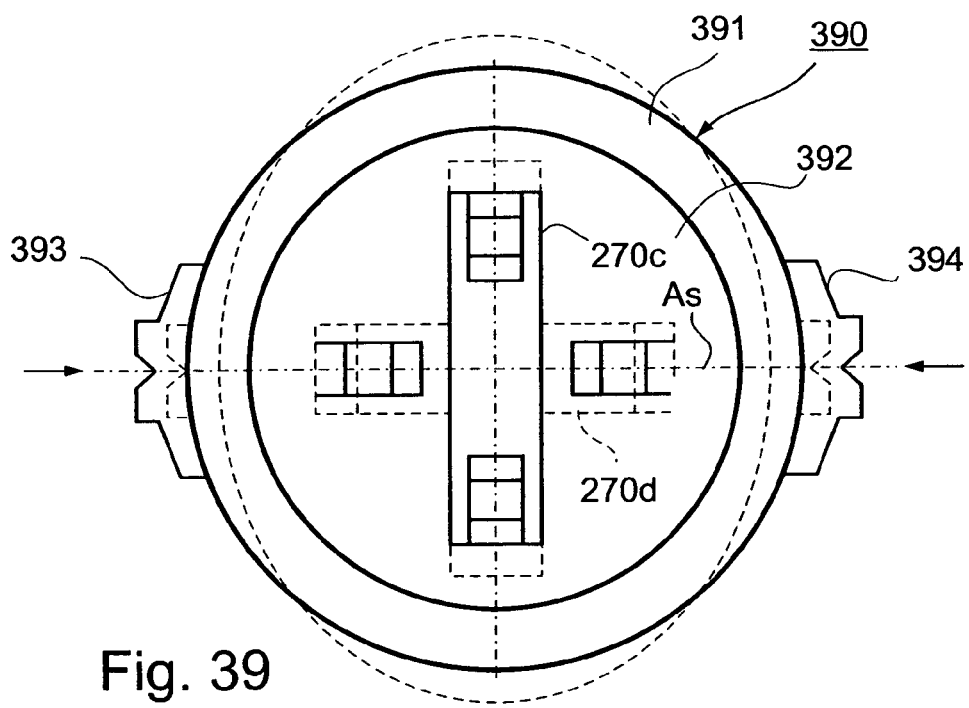
FIG. 39 is a plan view illustrating a temperature-compensated force sensor constructed in accordance with the present invention.

FIG. 39 is a plan view illustrating a force sensor 390 also constructed with two narrow acoustical channels of the type described above with respect to FIG. 27 to produce a temperature-compensated measurement of force. The force sensor 390 illustrated in FIG. 39 includes a mounting member 391 mounting a deformable member 392, such as a circular membrane (e.g., of rubber), which carries one narrow acoustical channel 270c on one face, and another narrow acoustical channel 270d on the opposite face, the latter therefore being shown in broken lines. The force to be measured is applied between two force-receiving members 393, 394, aligned with each other along an axis $A_S$, which defines the force-sensitive axis. Thus, when a compressive force is applied along axis $A_S$, the mounting member 391, as well as the circular membrane 392 on which the two acoustical channels 270c, 270d are mounted, is deformed as shown by broken lines in FIG. 39, such as to be contracted along the force-sensitive axis $A_S$, and to be expanded along the axis perpendicular to axis $A_S$.

As shown in FIG. 39, one acoustical channel 270d is mounted in alignment with axis $A_S$, whereas the other acoustical channel 270c is mounted along the axis perpendicular to axis $A_S$. Accordingly, acoustical channel 270c will increase in length according to the force applied, whereas acoustical channel 270d will decrease in length. The outputs of the two acoustical channels are connected in a subtractive manner as described above with respect to FIG. 16, such that the influence of the temperature cancels out, thereby making the sensor insensitive to temperature variations.

Figure 40A:
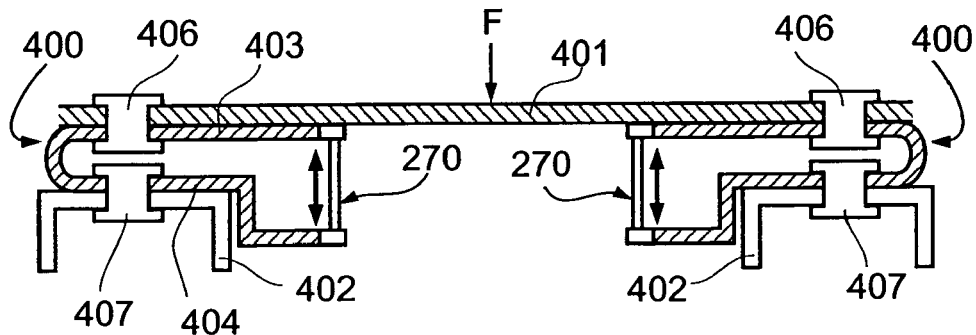
FIG. 40a illustrates another sensor constructed in accordance with the present invention particularly useful for measuring weight or certain other forces.
Figure 40B:
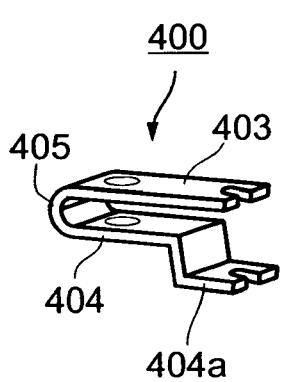

FIG. 40a illustrates a sensor assembly for use in measuring weight or other applied forces, whereas FIG. 40b illustrates one of the securing devices, generally designated 400, included in the sensor assembly of FIG. 40a. The weight or other force to be measured is applied to a panel 400, as shown by arrow F, of generally rectangular configuration and secured at each of its four corners by one of the securing devices 400 (two of which are shown in FIG. 40a). Each of the securing devices 400 includes a pair of parallel arms 403, 404, joined at one end by a U-bend 405. One of the arms 404 is formed with a stepped extension 404a at its open end to thereby increase the spacing between its open end 404a and the open end of the other arm 403. The U-bend end of arm 403 is secured by fastener 406 to plate 401 receiving the applied force, and the U-bend end of the other arm 404 is secured by another fastener 407 to the frame 402, such that the force F applied to panel 401 flexes the U-bend 405 of each of the securing devices 400.

A narrow-strip type sensor of the construction illustrated in FIG. 27, therein generally designated 270, is secured between arm 403 and the extension 404a of arm 404 at the open end of each of these securing devices 400. Each sensor 270 is of the construction described above with respect to FIG. 27, to include an acoustical channel of elastomeric material between a sonic transmitter and a sonic receiver, such that the contraction (or elongation) of the acoustical channel provides a measurement of the force applied to the respective securing device 400.

Figure 41:
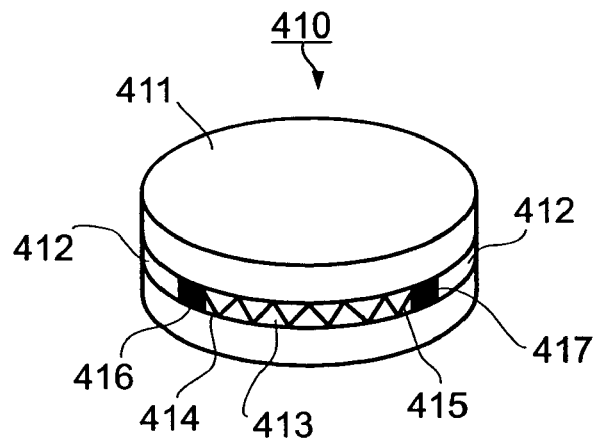
FIG. 41 is a three dimensional view illustrating another sensor constructed in accordance with the present invention particularly useful for measuring or detecting extremely small forces, such as those resulting from respiratory activity or cardiac activity.

FIG. 41 illustrates another narrow-strip type sensor, therein generally designated 410, constructed in accordance with the present invention. In this case, the narrow-strip sensor is fixed to the outer surface of a body 411 of pressure-deformable material of cylindrical configuration to extend around at least a part of the circumference of the body. Thus, as shown in FIG. 41, the body of pressure deformable material 411 is formed with an annular recess 412 midway between its opposite faces and extending for at least a part of its circumference. Fixed within recess 412 is a narrow-strip type sensor of the construction illustrated in FIG. 27, including a narrow strip 413 of an elastomeric material, a transmitter 414 at one end, and a receiver 415 at the opposite end. Preferably, the sensor further includes, at its opposite ends, damper elements 416, 417 of a sound absorbing material to suppress reflected sonic waves and to confine the sonic waves generated by the transmitter 414 to the narrow strip 413 of the elastomeric material.

It will thus be seen that when pressure is applied to the opposite faces of the cylindrical body 411, the body decreases in thickness and increases in diameter, thereby increasing the length of the acoustical channel 413 between the transmitter 414 and receiver 415. This increase in the transit distance of the acoustical channel thus enables a detection and measurement of the applied force to be made in the manner described above.

The pressure deformable body 411 may be of rubber or other sound absorbing material. In addition, the narrow sensor strip 413 could extend for substantially the complete circumference of body 411, but the transmitter should be spaced from the receiver, on the side opposite to that of the sensor channel 413, by sound absorbing material so as to substantially confine the sonic waves to the sonic channel defined by the elastomeric strip 413.

Figure 43:
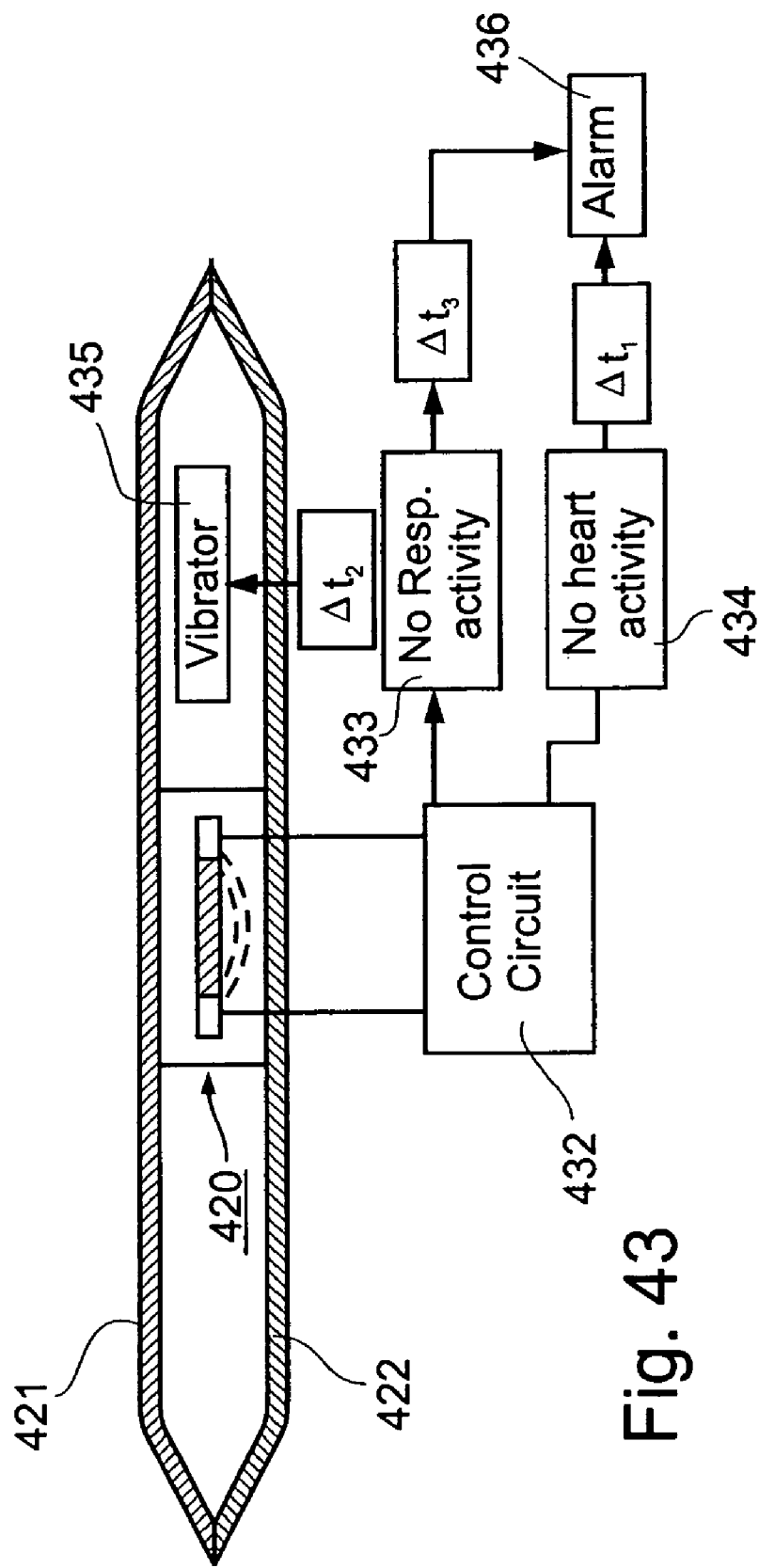
FIG. 43 illustrates an apnea monitor apparatus including the sensor of FIG. 42 for sensing both respiratory and cardiac activity and controlling a vibrator and/or alarm in response thereto.

Sensor 410 illustrated in FIG. 41 may be used in many of the above-described applications but is particularly useful in an apnea monitor, as illustrated in FIG. 43, to monitor both cardiac and respiratory activity of a person.

Figure 42:
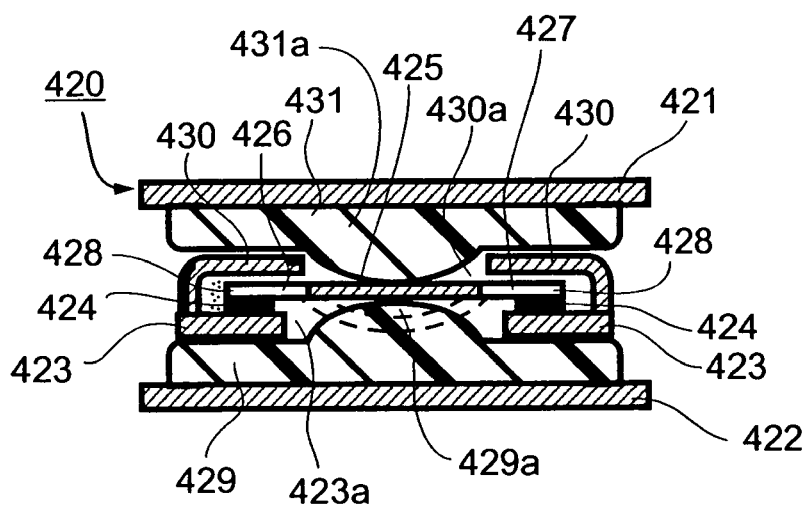
FIG. 42 is a sectional view illustrating yet another sensor constructed in accordance with the present invention.

FIG. 42 illustrates another sensor constructed in accordance with the present invention and particularly useful in an apnea monitor, as illustrated in FIG. 43. Thus, as shown in FIGS. 42 and 43, the sensor, therein generally designated 420, is mounted between a pair of plates 421, 422, which may be applied over, under, or within a mattress occupied by a person (e.g., a baby, elderly patient, etc.) whose cardiac activity and respiratory activity are to be monitored. Sensor 420 includes a printed circuit board 423 formed with an opening 423a straddled by a pair of electrical-conductive pads 424. An acoustical-channel type sensor including a strip of elastomeric material 425 having a sonic transmitter 426 at one end and a sonic receiver 427 at the opposite end, is applied over the electrically-conductive pads 424 to overlie the opening 423a in the printed circuit board 423. The electrical connections to the sonic transmitter and sonic receiver are connected by solder 428, to the conductive pads 424.

The printed circuit board 423, with the elastomeric acoustical channel 425 secured thereto, is supported on a body of rubber or other sound absorbing material, having a projection 429a projecting through opening 423a in the printed circuit board so as to support the underface of the elastomeric strip 425. The printed circuit board 423 further includes a rigid cap 430 overlying the sonic transmitter and sonic receiver of the elastomeric strip 425 and formed with a central opening 430a exposing the upper side of the elastomeric strip 425. Another body of rubber or other sound absorbing material 431 is interposed between cap 430 and the other panel 421, and is formed with a projection 431a projecting through the opening 430a in cap 430 to engage the upper side of the elastomeric strip 425.

It will thus be seen that any force applied to plate 421 will deflect the elastomeric strip 425, as shown in broken lines in FIG. 42, to thereby increase the effective length of the elastomeric strip, and thereby the transit time of a sonic wave from its transmitter 426 to its receiver 427, such as to provide a measurement of the applied force in the manner described above.

As indicated above, sensor 420 of FIG. 42 (as well as sensor 410 of FIG. 41), particularly when included in an apnea monitor as illustrated in FIG. 43, is so sensitive to applied forces as to be able to detect not only respiratory activity and other motions by the person, but also heart activity of the person. Thus, as shown in FIG. 43, the output of sensor 420 can be applied to a control circuit 432, which can thereby detect both the lack of respiratory activity, as shown by block 433, or the lack of heart activity, as shown by block 434.

The illustrated apnea monitor thus includes a vibrator 435, which is actuated when necessary to stimulate the person, and an alarm 436 which may be actuated to notify another of an alarm condition. Thus, as shown in FIG. 43, if no heart activity is detected for a predetermined period of time ($t_1$, e.g., five seconds), alarm 436 is immediately actuated. On the other hand, if no respiratory activity is detected for a predetermined interval ($t_2$, e.g., twenty seconds), vibrator 435 is actuated in an attempt to stimulate the person; and if the lack of respiratory activity continues for another time interval ($t_3$, e.g., an additional ten seconds), the alarm 436 is actuated.

It will be appreciated that such an apnea monitor could be provided for a single person, (e.g., baby, elderly patient); on the other hand, where two persons (e.g., elderly persons) occupy a double bed, two such apnea monitors could be provided, one for each person, so as to actuate an alarm to alert the other person whenever an alarm condition is found to be present.

It will be appreciated that the sensor illustrated in FIG. 42, as well as the apnea monitor illustrated in FIG. 43, may be used in many other applications, e.g., in the bed sore preventing apparatus or in the anti-snoring apparatus, described earlier.

Because of the extremely high sensitivity attainable by the sensors of the present invention in detecting and measuring extremely small displacements or micro-displacements, such sensors are particularly useful for synchronizing the operation of imaging systems in accordance with the respiratory and/or cardiac activity of the patient.

Thus, the detailed images produced by magnetic resonance imaging (MRI) systems are often blurred by the motion of the patient during cardiac and respiratory cycles. The patient's ECG signals are frequently used as gating signals for synchronizing the operation of the MRI apparatus, but ECG signals do not closely correlate with the mechanical motion causing the blurring. Finger probes have also been used for this purpose for detecting pulsatile blood flow, but the use of such sensors also introduces a time delay between the motions caused by the heart activity and the sensing of the blood pulse.

Sensors constructed in accordance with the present invention are particularly useful for directly sensing extremely small displacements arising from cardiac activity and/or respiratory activity in order to produce gating signals synchronizing the operation of the MRI apparatus in accordance with such detected movements, and thereby to minimize or eliminate blurring of the images produced by such movements. For example, an acceleration-type sensor as described above may be applied to the person's chest to detect cardiac activity; and/or a displacement type sensor as described above may be applied against the patient's chest, as by an elastic belt, or under the patient's body supporting member, for detecting respiration activity of the patient. By using such sensors for detecting micro-displacements of the patient arising from cardiac and/or respiratory activity and for producing gating signals for synchronizing the operation of the MRI apparatus, the blurring produced by body motion during an imaging operation can be minimized or eliminated to produce much clearer images than those heretofore attainable by ECG or pulsatile blood signals.

While sensors constructed in accordance with the invention are thus particularly useful for MRI procedures, they are also useful in other types of imaging, including CT, PET, nuclear, ultrasonic, and X-ray imaging.

In addition, while such sensors are particularly useful for detecting heart and respiration activity, and for synchronizing the operation of the imaging system in accordance with such detected activity, it will be appreciated that such sensors could also be used for detecting other activities of the patient, such as stomach movements, stone movements in a kidney, etc. and used for synchronizing the operation of the imaging system in accordance therewith.

Figure 44:
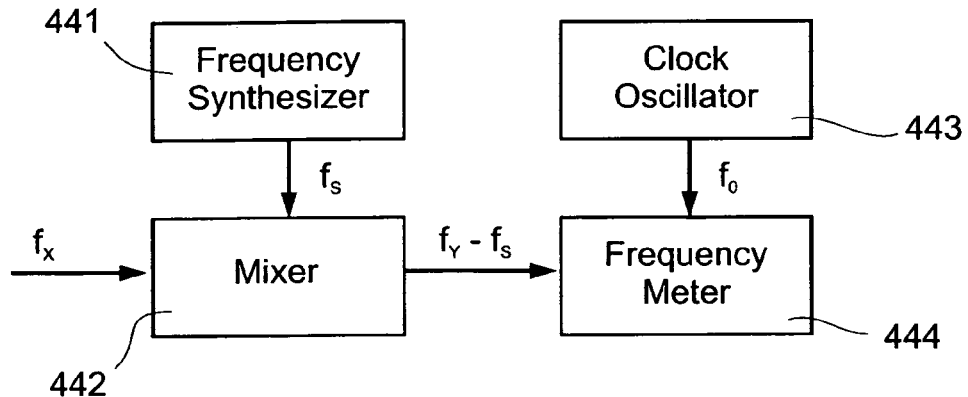
FIG. 44 is a block diagram illustrating an improved frequency-measurement system particularly useful in apparatus constructed in accordance with the present invention.
Figure 45:
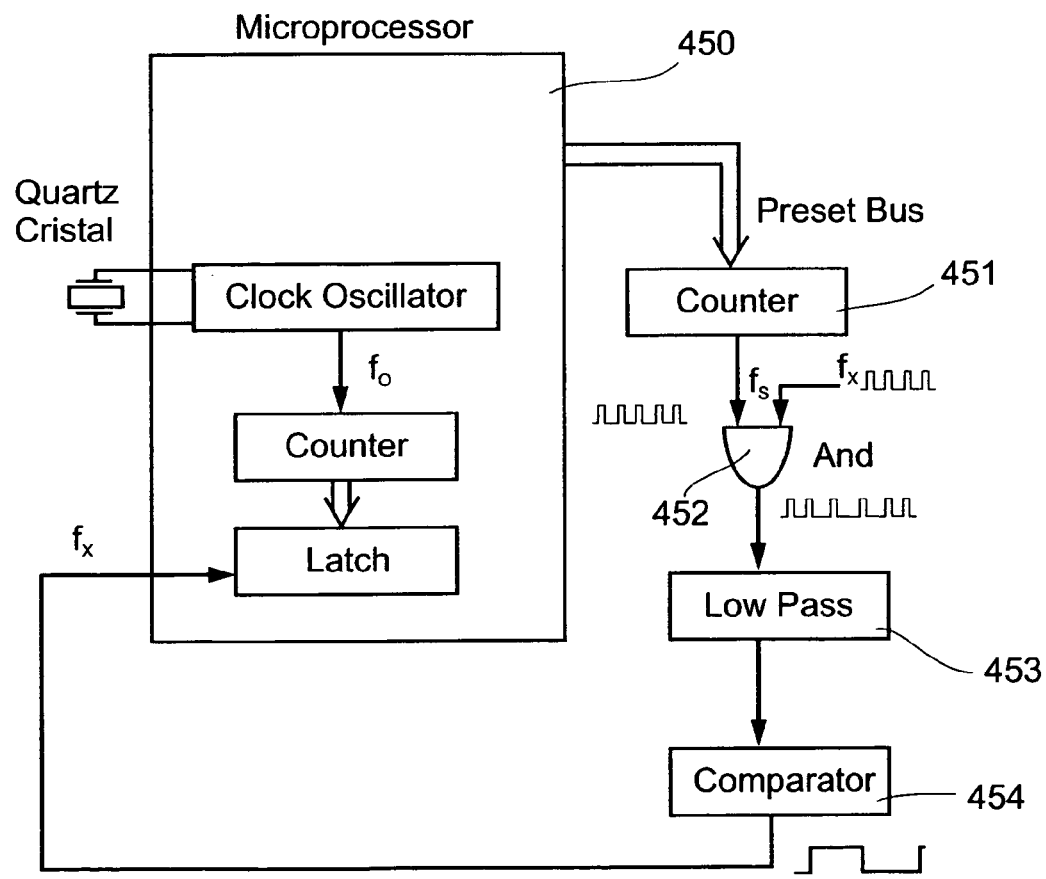
FIG. 45 is a block diagram more particularly illustrating the frequency-measurement system of FIG. 44.
Figure 46:
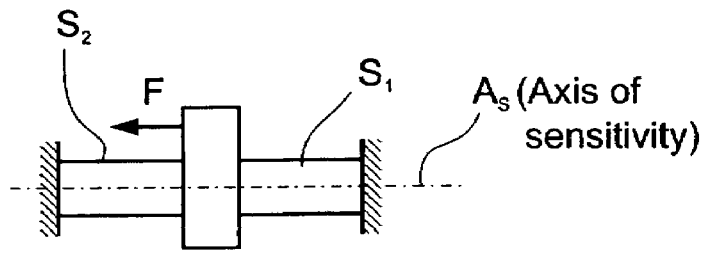
FIG. 46 is a diagram illustrating an implementation of the invention to provide for temperature-compensation.
Figure 47:
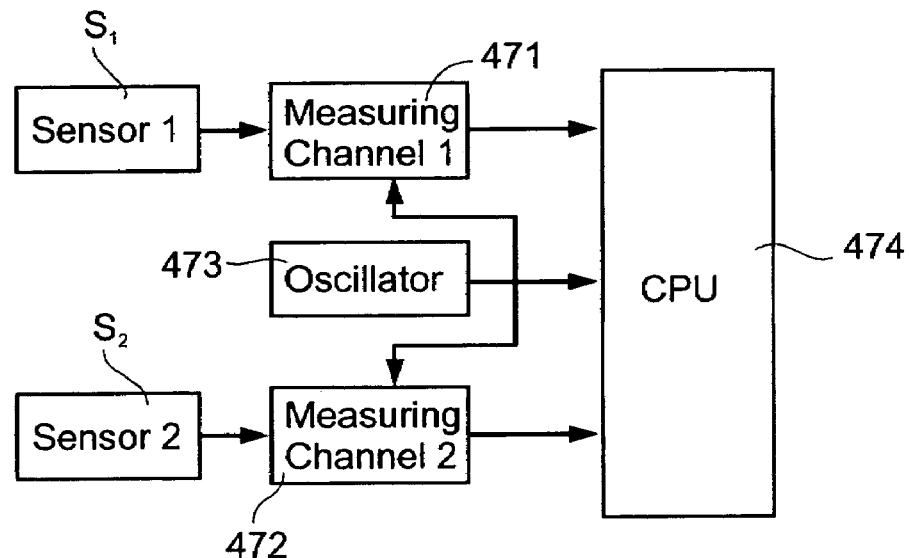
FIG. 47 is a block diagram illustrating a system constructed in accordance with FIG. 46 to provide temperature compensation.
Figure 48:
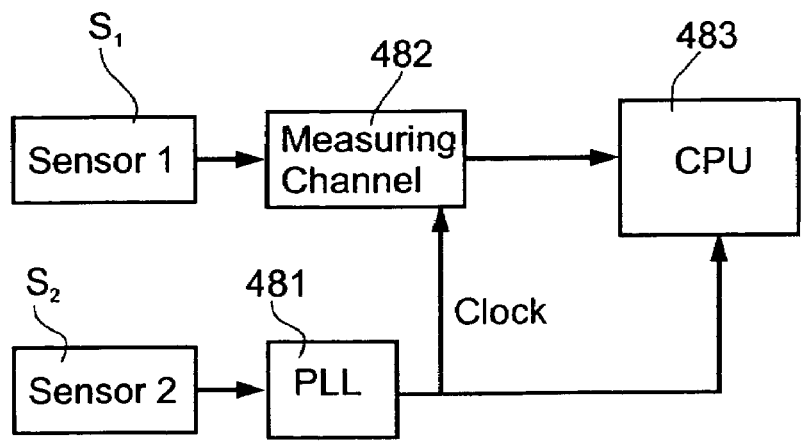
FIG. 48 illustrates an improved system constructed in accordance with FIG. 46 to provide temperature-compensation.
Figure 49:
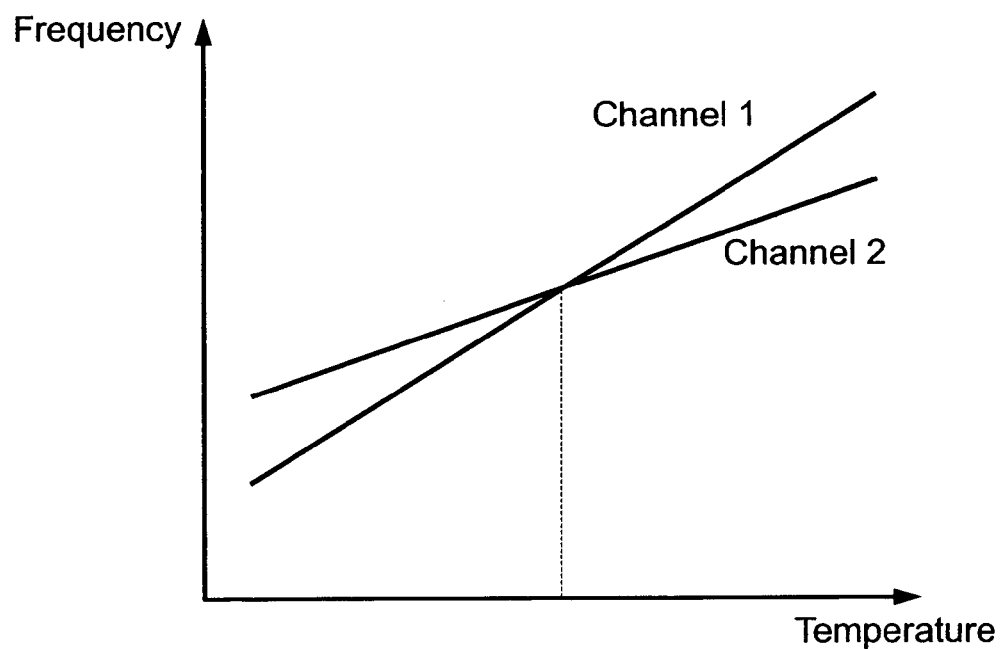
FIG. 49 is a diagram helpful in explaining one manner of implementing the invention as a highly stabilized frequency generator.

FIGS. 44-50 illustrated further features useful with respect to the sensors and systems utilizing such sensors described above. Thus FIGS. 44 and 45 relate to a novel frequency-measurement circuit and method; FIGS. 46-48 relate to a novel temperature-compensation circuit and method; and FIGS. 49 and 50 relate to a novel frequency-generation circuit and method.

With respect to the frequency measurement circuits of FIGS. 44 and 45, the conventional method to measure time intervals with high resolution is to use high frequency clock oscillators. However, conventional oscillators are expensive and have large current consumption, which detract from their use in low power and low cost applications of the above-described sensor system.

In the method of FIG. 2, assume the frequency $f_x$ in a feed back loop is 1 MHz (i.e., period is 1 μsec); the measuring time is 10 msec; and the clock frequency is 100 MHz (i.e., clock period or resolution is 10 nsec). Actually, a duration of 10 msec/1 μsec (10,000 periods) is measured, enabling distinguishing changes in a total duration of 1 nsec, or in a period of 1 nsec ($10,000=10^{-4}$ nsec), i.e., differences between periods of 10 μsec and 0.9999999 μsec will be distinguishable. This corresponds to a frequency difference of 0.1 Hz for 1 MHz. Such a system permits very high resolution, but a 100 MHz clock results in the disadvantages described above.

Now consider the same measurement conditions, i.e., a measured frequency of 1 MHz, a deviation of 0.1 Hz, and a measuring time of 10 msec. FIG. 44 illustrates a measurement circuit for this purpose, which consists of followed units: a reference frequency synthesizer 441; a frequency mixer 442; a clock oscillator 443; and a measuring unit 444.

Assume the synthesizer 441 produces a frequency $f_s$=999.5 kHz. Thus, the output of mixer will be 1 MHz-999.5 kHz=500 Hz without deviation, and 1.0000001 MHz-999.5 kHz=500.1 Hz with 0.1 Hz deviation of the measured frequency.

A frequency of 500 Hz corresponds to a period of 2 msec, and a frequency of 500.1 Hz corresponds to 1.9996 msec. If a duration of 5 periods (10 msec) is to be measured, and the difference 5·(2 msec-1.9996 msec), (or 0.002 msec) is to be distinguished, a clock 383m with this period (0.002 msec) is needed, which corresponds to a frequency of 500 kHz.

Thus it is possible to use a low frequency clock 443 (e.g., 500 Khz) instead of a 100 MHz clock, to provide the same resolution. On the other hand, the clock may be increased, (e.g., up to the relative low value of 5 MHz) to reduce the measuring time (e.g., to 1 msec).

FIG. 45 illustrates a manner in which the frequency meter and the clock oscillator may be realized in a microprocessor 450 with a capture feature, i.e., each edge of measured frequency may control the internal latch register in order to fix the state of the internal counter which is clocked with the internal clock oscillator. The processor calculates all the time difference between successive stages of the latch register.

The synthesizer (451, FIG. 45) may be realized as a counter 451 of the clock oscillator output pulses, and its frequency may be controlled with a preset signal from the microprocessor. The mixer (452, FIG. 45) may be realized as the digital AND-logic element 452 with a low pass analog filter 453 and comparator 454. Like any non-linear unit, the AND-logic element 452 creates difference and summation frequencies on its output. The low pass filter 453 extracts just the difference sinusoidal frequency, The comparator 454 creates square pulses which are received with the frequency meter 444 (FIG. 44).

With respect to FIGS. 46-48 illustrating the temperature compensation feature, the temperature influences the speed of energy propagation and initiates thermal expansion which, as noted above, results in changes of the transit time between the transmitter and the receiver. Because of the very high sensitivity of the above-described sensor systems, there may be considerable temperature drift in the output frequency. When one measures the signals which changes slowly, it is very difficult to distinguish between a signal change and a temperature drift.

Temperature drift may be eliminated by a two-channel measurement as described above with respect to FIGS. 16 and 44. FIG. 46 illustrates such a two-channel measurement system including the two sensors $S_1$, $S_2$ to measure force. As shown in FIG. 46, the force to be measured acts to expand one sensor $S_1$ and to contract sensor $S_2$. Thus the output frequency of sensor $S_2$ will be increased (+$\Delta f$) and that of sensor $S_1$ will be decreased (−$\Delta f$). The final output signal is developed by subtracting one output frequency from the other:

$$F=f_1 f_2=(f_0+\Delta f+\Delta f_T)-(f_0-\Delta f+\Delta f_T)=2\Delta f$$

Since the temperature drift results in the same changes ($\Delta f_T$) in both channels, the subtraction will eliminate changes caused by temperature drift.

Actually in the standard method as shown in FIG. 47, each measuring channel 471, 472 measures the ratio of the input frequency and the clock. The standard method uses a special clock oscillator 473 for both measuring channels and for the processor 474. A disadvantage of the above-described method, therefore, is that it needs to use two separate measuring channels, and to allocate processor time to perform the subtraction algorithm.

FIG. 48 illustrates an improved method in which one sensor $S_1$ is used for the single measuring channel, and the second sensor $S_2$ is connected to the input of a phase-locked loop (PLL) circuit 481. The high frequency output of the PLL circuit 481 is used as the clock of both the measuring channel 482 and the processor 483. When the temperature changes, the frequencies of the measuring channel and the clock are changed proportionally. Thus its ratio is not changed since the applied force produces opposite changes of frequencies, and thereby opposite changes in the above ratio:

$$R=\frac{Fchannel}{Fcloc}=\frac{f_0+\Delta f+\Delta f_T}{f_0-\Delta f+\Delta f_T}\approx 1+\frac{2\Delta f}{f_0}$$

It is to be noted that the ratio need not be calculated in the processing unit; rather it is automatically reflected in the output of the measuring channel.

As indicated above, this technique also enables the construction of a new frequency-generator. It is to be noted that crystal oscillators used in existing frequency generators usually consist of a single quartz crystal with two electrodes which are connected to an electrical feed-back circuit. The oscillation frequency is determined by the mechanical resonance of the crystal, which is much more stable than the resonance frequency of electrical circuits with capacitance and inductance. A disadvantage of such oscillators is that the crystal operates simultaneously as an electromechanical transducer and as a mechanical resonator. It is very difficult to combine different requirements in one material, e.g., high electromechanical coupling of a transducer, and temperature stability of a resonator. Regardless of the fact that quartz is considered as a very good material for oscillators, for many applications its temperature stability is not sufficient.

The novel sensors described above are capable of providing a frequency generator having very high temperature stability since frequency of oscillation depends on the properties and geometry of the channel material rather than of the piezo-transmitter and receiver. Thus it is possible to choose the most suitable materials separately for the mechanical resonator and for the electromechanical transducers.

Suppose a system includes two acoustical channels as described above with each channel having a transmitter and a receiver controlling the transmitter to transmit an integer member of sonic waves to the receiver, and with electrical feedback. Each channel is produced from material having a low coefficient of linear expansion, which coefficient differ slightly in the two channels. Consequently, when the temperature changes, the integer number of sonic waves in each channel, and thereby the frequency of each channel, will be changed. As shown in FIG. 45, there is a certain temperature point where the channel frequencies are equal and where changes in temperature produce opposite changes in frequency.

Figure 50:
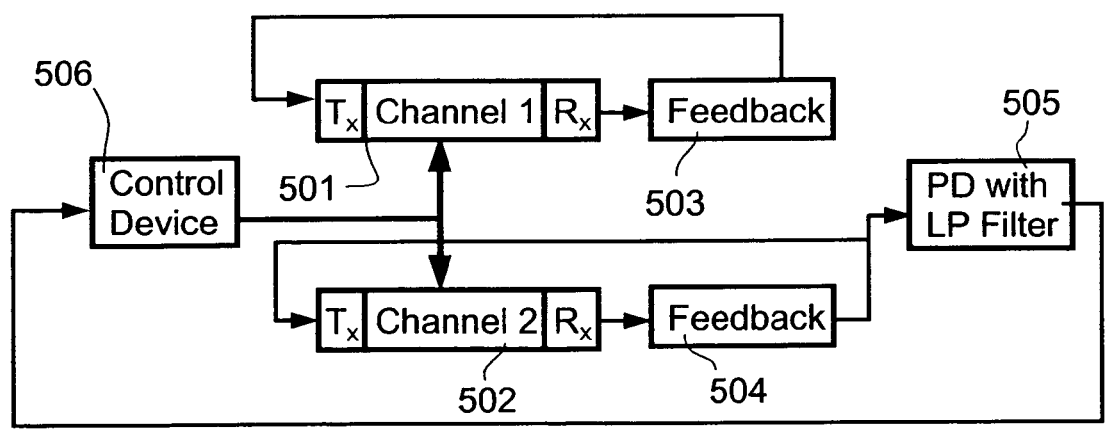
FIG. 50 is a block diagram illustrating a frequency-generator circuit constructed in accordance with the diagram of FIG. 49.

FIG. 50 illustrates such a system including the two channels 501, 502 and their feedbacks 503, 504, but provided with an additional feedback consisting of a phase detector 505 with a low pass filter, and a control device 506. The inputs of the phase detector 505 are the outputs of the two channels 501, 502. The output of the control device 506 forces both channels to change their lengths identically and simultaneously.

At a certain temperature point, when the frequencies are equal, the output of the phase detector 505 is zero, and the control device 506 does not influence the channel. When the temperature is changed, both frequencies attempt to change. This will immediately produce a difference of phases in the outputs of the two channels because of the slightly different temperature sensitivity of the channels. The output signal applied by the phase detector 505 to the control device 506 will force the channels to change length in such manner to equalize both of the frequencies. Thus both frequencies will return to the stabilization point.

Control device 506 may be implemented in different forms including the following:

1. It may be embodied in a heating device. In this case a stable temperature point is chosen higher than the maximum working temperature. Thus when the environmental temperature is changed, the temperature of both channels is kept at a point where the frequencies are equal; i.e., the above-mentioned additional feedback is actually a thermo-stabilization device.

2. It may be embodied in an electromechanical actuator. In this case, the control device will produce an expansion or contraction of both channels with the ratio corresponding to their temperature coefficients. Thus, when the environmental temperature is changed, the length of both channels is kept at a point where the frequencies are equal.

Such an actuator may be implemented in different forms: as a piezo-electric actuator, which changes its length according to the reverse piezoelectric effect when voltage is applied on its electrodes; as a magnetostrictive actuator, which changes its length according to the magnetostriction effect when electrical current flows in its coil; or as any other actuator, which produces a displacement according to its electrical input.

While the above-described features as illustrated in FIGS. 44-50 are particularly useful with respect to sensors and systems constructed in accordance with the present invention as illustrated in FIGS. 1-43, it will be appreciated that such features are also useful in other applications where frequency-measurement, temperature compensation, and/or frequency generation is also involved.

Also, while the invention has been described with respect to various preferred embodiments, it will be appreciated that these are set forth merely for purposes of example, and that many other variations and applications of the invention may be made. For example, a sensor assembly may include not only one of the above-described axially-extending sensors (e.g., FIGS. 1-9), transversely-extending sensors (e.g., FIGS. 34-36 and 42), or circumferentially-extending sensors (e.g., FIG. 41), for detecting changes in the transit distance of the acoustical channel in response to the condition being detected, but may also include a temperature-sensitive element, such as shown in FIG. 8, which changes the transit velocity of the acoustical wave in response to the condition being detected. In addition, while the preferred embodiments of the invention described above utilize sonic transmitters and receivers, it will be appreciated that the sensor could also be implemented with transmitters and receivers of visible light, infrared, RF or other electromagnetic energy.

Many other variations, modifications and applications of the invention will be apparent.

What is claimed is:

1. Apparatus for measuring a predetermined parameter having a known or determinable relationship with respect to the transit time of an energy wave through a medium, comprising:

a sensor for sensing said predetermined parameter, said sensor including a transmitter for transmitting energy waves through said medium and a receiver for receiving said energy waves transmitted by said transmitter;

and a data processor for measuring the transit time, or changes in the transit time, of energy waves from said transmitter to said receiver to thereby produce a measurement of said predetermined parameter;

characterized in that said sensor includes a body of soft elastomeric material having high transmissivity and low attenuation properties with respect to said energy waves, said transmitter and receiver being embedded in spaced relation to each other in said body of soft elastomeric material to define a transmission channel constituted of the elastomeric material between said transmitter and reciever, such that said parameter, when sensed by said sensor, produces a displacement of said transmitter relative to said receiver, whereby measuring the transit time, or changes in the transit time, of said energy waves through said transmission channel from said transmitter to said receiver provides a measurement of the displacement of the transmitter relative to the receiver, and thereby of said predetermined parameter.

2. The apparatus according to claim 1, wherein said elastomeric material is a silicone elastomer.

3. The apparatus according to claim 1, wherein said elastomeric material has a Shore A hardness of 5-60.

4. The apparatus according to claim 1, wherein said elastomeric material has a Shore A hardness of 7-20.

5. The apparatus according to claim 1, wherein said energy wave is a sonic wave.

6. The apparatus according to claim 1, wherein the apparatus includes two of said sensors mounted on a common support with one of their ends facing and aligned with each other, and their opposite ends fixed to said support; said facing ends of the sensors being fixed to a member located between them and displaceable by said predetermined parameter towards one sensor and away from the other sensor, such that the displacement of said displaceable member in either direction compresses the elastomeric body of one sensor and expands the elastomeric body of the other sensor, thereby substantially eliminating temperature and other transient influences, while enhancing the measurement of said predetermined parameter.

7. A sensor for sensing a predetermined parameter having a known or determinable relationship with respect to the transit time of an energy wave through a medium, comprising:
  a body of soft elastomeric material having high transmissivity and low attenuation properties with respect to said energy waves;
  and a transmitter and receiver carried by said body in spaced relation to each other to define an acoustical transmission channel constituted of the elastomeric material between said transmitter and receiver, such that the energy waves received by said receiver are those transmitted by said transmitter through said acoustical transmission channel after having traversed at least a portion of said body of soft elastomeric material.

8. The sensor according to claim 7, wherein said elastomeric material is a silicone elastomer.

9. The sensor according to claim 7, wherein said elastomeric material has a Shore A hardness of 5-40.

10. The sensor according to claim 7, wherein said elastomeric material has a Shore A hardness of 7-20.

11. The sensor according to claim 7, wherein said energy wave is a sonic wave.

12. The sensor according to claim 7, wherein said transmitter and receiver are embedded in said body of elastomeric material.

13. The sensor according to claim 7, wherein said body of elastomeric material includes an array of said transmitters and receivers for use as a keyboard or pressure-distribution sensor.

14. The sensor according to claim 7, wherein said body of elastomeric material is of annular shape for receiving a finger, wrist or arm of a person.

15. The sensor according to claim 7, wherein said sensor also includes a weight which acts as an inertia member effective to make the sensor sensitive to the rate of change of the spacing between said transmitter and receiver.

16. The sensor according to claim 15, wherein said weight is carried by a pivotably mounted arm.

17. The sensor according to claim 7, wherein said body of soft elastomeric material is in the form of a narrow strip such as to define a narrow transmission channel between said transmitter and receiver.

18. The sensor according to claim 17, wherein said energy wave is a sonic wave and said narrow transmission channel is a narrow acoustical channel.

19. The sensor according to claim 18, wherein said sensor further includes a damper material having high sonic-wave attenuation properties at the opposite ends of said strip of soft elastomeric material, said damper material being effective to absorb sonic waves except those in said narrow acoustical channel.

20. Apparatus according to claim 1, wherein said apparatus is in the form of a hand-held portable electrical device comprising a housing carrying said sensor for enabling the device also to be used for measuring said predetermined parameter.

21. The apparatus according to claim 20, wherein said hand-held device is a cellular telephone handset or portable digital assistant.

22. Apparatus according to claim 1, wherein said data processor includes a frequency measuring circuit, comprising:
  a frequency synthesizer generating a predetermined frequency;
  a mixer having one input receiving said predetermined frequency of the synthesizer, and a second input receiving the frequency of transmission by said transmitter of the sensor, and for producing an output frequency in which the frequency of one input is subtracted from that of the other input;
  a clock oscillator for generating a clock frequency;
  and an output circuit having one input receiving the output of said mixer, and a second input receiving the output of said clock oscillator for producing a measurement of the frequency of transmission by said transmitter of the sensor.

23. Apparatus according to claim 6, wherein said data processor includes:
  a single measuring channel having an input from one sensor and an output to a CPU;
  and a phase-locked loop having an input from the other sensor, and an output providing clock pulses to said single measuring channel and to said CPU.

24. A system for generating a predetermined frequency, comprising:
  first apparatus according to claim 1 including a first body of soft elastomeric material defining a first acoustical channel of a first effective length and having a first coefficient of linear expansion in response to temperature;
  a second apparatus according to claim 1 including a second body of soft elastomeric material defining a second acoustical channel of a second effective length and having a second coefficient of linear expansion in response to temperature different from said first coefficient of linear expansion;
  a first electrical feedback circuit from said first apparatus for controlling the frequency thereof;
  a second electrical feedback circuit from said second apparatus for controling the frequency thereof;
  a phase detector with a low pass filter receiving the outputs of said first and second electrical feedback circuits;
  and a control device controlling said first and second bodies of soft elastomeric material in response to the output of said phase detector to cause both bodies of soft elastomeric material to change their effective lengths such as to equalize the frequencies of both acoustical channels.

25. A system for generating a predetermined frequency, comprising:
  a first acoustical channel having a transmitter and a receiver controlling the transmitter to transmit an integer number of sonic waves to the receiver, said first acoustical channel having a first effective length and a first coefficient of linear expansion in response to temperature;

a second acoustical channel having a transmitter and a receiver controlling the transmitter to transmit an integer number of sonic waves to the receiver, said second acoustical channel having a second effective length and a second coefficient of linear expansion in response to temperature;

a first electrical feedback circuit from said first acoustical channel to control the frequency thereof a second electrical feedback circuit from said second acoustical channel to control the frequency thereof;

a phase detector receiving the outputs of said first and second electrical feedback circuits;

and a control device controlling said first and second acoustical channels in response to the output of said phase detector to equalize the frequencies of the two acoustical channels.

26. The system according to claim 25, wherein said phase detector has a low-pass filter.

27. The system according to claim 25, wherein each of said acoustical channels includes a body of soft elastomeric material having high sonic-wave transmissivity and low sonic-wave attenuation.

* * * * *